US008728545B2

(12) United States Patent
Chabot et al.

(10) Patent No.: US 8,728,545 B2
(45) Date of Patent: May 20, 2014

(54) **EXTRACTION METHOD FOR PROVIDING AN ORGANIC CERTIFIABLE *STEVIA REBAUDIANA* EXTRACT**

(75) Inventors: Sophie Chabot, St-Jean-Port-Joli (CA); Martin Beaulieu, Quebec (CA)

(73) Assignee: Justbio Inc., Lapocatiere (Quebec) (CA)

( * ) Notice: Subject to any disclaimer, the term of this patent is extended or adjusted under 35 U.S.C. 154(b) by 0 days.

(21) Appl. No.: 13/809,430

(22) PCT Filed: Jul. 13, 2011

(86) PCT No.: PCT/CA2011/050433
§ 371 (c)(1),
(2), (4) Date: Jan. 10, 2013

(87) PCT Pub. No.: WO2012/006742
PCT Pub. Date: Jan. 19, 2012

(65) Prior Publication Data
US 2013/0108718 A1    May 2, 2013

Related U.S. Application Data

(60) Provisional application No. 61/441,365, filed on Feb. 10, 2011, provisional application No. 61/365,032, filed on Jul. 16, 2010.

(51) Int. Cl.
*A01N 65/00*    (2009.01)

(52) U.S. Cl.
USPC ........................................................ 424/725

(58) Field of Classification Search
None
See application file for complete search history.

(56) References Cited

U.S. PATENT DOCUMENTS

| 5,972,120 | A | 10/1999 | Kutowy et al. |
| 2006/0142555 | A1 | 6/2006 | Jonnala et al. |
| 2007/0082103 | A1 | 4/2007 | Magomet et al. |
| 2011/0091617 | A1 | 4/2011 | Abelyan et al. |

FOREIGN PATENT DOCUMENTS

| CA | 2185496 | 3/1998 |
| JP | 52100500 | 8/1977 |
| JP | 54030199 | 3/1979 |
| JP | 55081567 | 6/1980 |
| JP | 55111768 | 8/1980 |
| JP | 58212759 | 12/1983 |
| JP | 58212760 | 12/1983 |
| JP | 59042862 | 3/1984 |
| JP | 6007108 | 1/1994 |
| KR | 900007421 B1 | 10/1990 |
| RU | 2198548 C1 | 2/2003 |

OTHER PUBLICATIONS

Amberlite XAD-2 Polymeric Adsorbent—Product Specification, Supelco, T497172, 1997 Sigma-Aldrich Co.
Rohm and Haas, Ion Exchange Resins, Product Data Sheet, AmberliteTM IRA900 Cl, Industrial Grade Strong Base Anion Exchanger, 2008 Rohm and Haas Company, PDS 0295 A—Jan. 2008.
Jumpatong, Kanlaya et al., "Dechlorophyllation by Electrocoagulation," Molecules 2006, 11, 156-162.
Kinghorn, et al., "Current Status of Stevioside as a Sweetening Agent for Human Use," Economic and medicinal Plant Research, 1995, pp. 1-52.
Brandle, et al , "*Stevia refaudiana*; Is Agricultural, Biological, and Chemical Properties;" Agriculture and Agri-Food Canada, Apr. 28, 1998, pp. 527-536.
Philips, "*Stevia*: Steps in Developing a New Sweetner."Developments in Sweeteners, 1989, pp. 1-43.
International Preliminary Report on Patentability for PCT/CA2011/050433 completed May 16, 2012.
International Search Report for PCT/CA2011/050433 mailed Oct. 13, 2011.

*Primary Examiner* — Michael Meller
(74) *Attorney, Agent, or Firm* — Sutherland Asbill & Brennan LLP

(57) ABSTRACT

A simple extraction method for preparing an organic certifiable *stevia* extract with high sweetness and optionally with antioxidant properties is provided. The extraction method involves extraction of *stevia* leaves that have been dried and grinded with a hot solvent generally regarded as safe (GRAS), allowing the dissolution of the sweetening compounds naturally present therein. These sweetening compounds include steviosides and rebaudioside A, which are purified from the extracts by two or more successive chromatographic purifications steps. The sweetening compounds are then eluted with an appropriate elution solvent. The simplicity and organic certification of the method provide advantages over the methods currently employed in the *stevia* industry.

22 Claims, 17 Drawing Sheets

| Compound Names | R1 (C-19) | R2 (C-13) |
|---|---|---|
| 1 Steviol | H | H |
| 2 Steviolbioside | H | β-Glc-β-Glc(2→1) |
| 3 Stevioside | β-Glc | β-Glc-β-Glc(2→1) |
| 4 Rebaudioside A | β-Glc | β-Glc-β-Glc(2→1) |
|  |  | β-Glc(3→1) |
| 5 Rebaudioside B | H | β-Glc-β-Glc(2→1) |
|  |  | β-Glc(3→1) |
| 6 Rebaudioside C (dulcoside B) | β-Glc | β-Glc-α-Rha(2→1) |
|  |  | β-Glc(3→1) |
| 7 Rebaudioside D | β-Glc-β-Glc(2→1) | β-Glc-β-Glc(2→1) |
|  |  | β-Glc(3→1) |
| 8 Rebaudioside E | β-Glc-β-Glc(2→1) | β-Glc-β-Glc(2→1) |
| 9 Rebaudioside F | β-Glc | β-Glc-β-Xyl(2→1) |
|  |  | β-Glc(3→1) |
| 10 Dulcoside A | β-Glc | β-Glc-α-Rha(2→1) |

EXTRACTION METHOD FOR PROVIDING AN ORGANIC CERTIFIABLE *STEVIA REBAUDIANA* EXTRACT

CROSS REFERENCE TO RELATED APPLICATIONS

This application is a 371 US national stage application of International Application Number PCT/CA2011/050433 filed Jul. 13, 2011, which claims priority from U.S. provisional application 61/365,032 filed Jul. 16, 2010 and from U.S. provisional application 61/441,365 filed Feb. 10, 2011, the disclosures of which are incorporated herein by reference in their entireties.

FIELD OF THE INVENTION

The present invention relates to the fields of organic *stevia rebaudiana* extraction, zero or low calorie natural sweeteners. More specifically, the present invention relates to an extraction method for providing an organic certifiable *stevia* extract. In a particular embodiment, a solvent-less extraction method is described.

BACKGROUND OF THE INVENTION

Sweeteners are widely used both by consumers and by the food and beverage industry. Consumers use them as an ingredient in various food items and also as a means for customizing the sweetness of beverages, fruit, yogurt, and the like. The food and beverage industry uses such sweeteners in prepared beverages and other food items. Such sweeteners include both caloric and low-caloric sweeteners. Caloric sweeteners include sucrose, fructose, and glucose. Recently, low-calorie (or non-calorie) sweeteners have gained increased popularity. In many instances, they can be used as substitutes for caloric sweeteners and are often referred to as "sugar substitutes". Common sugar substitutes include saccharin, aspartame, and sucralose. In parts of Asia, compounds extracted from *stevia rebaudiana* (hereinafter *stevia*) plants have also been used as sugar substitutes for some time. For example, Japan has marketed *stevia* as an alternative to artificial sweeteners since 1970. In the 1980s, China began producing *stevia* commercially, becoming the main supplier to Japan.

There is an increasing interest for natural sweeteners. This interest stems partially from increasing consumer demand for such products, but also from the rise of a variety of businesses selling natural products and requiring suppliers of such products to certify that natural ingredients are used in any products being supplied.

Numerous extraction methods to produce *stevia* extracts rich in steviosides and rebaudioside A have been described. Most commercial processes used by the *stevia* industry consist of: water, solvent, and/or supercritical gas extraction; addition of multiple solvents and chemicals such as HCl, NaOH, $CaCO_2$, methanol, $H_3PO_4$, NaCl; decoloration (fading); purification using ion-exchange resins; electrolytic techniques; or precipitating agents involving numerous complex steps.

In general, the methods of preparing *stevia* extracts employed by the *stevia* industry are complex and involve numerous steps, which can be quite costly and time consuming. In addition, these methods have often been directed towards the separation of individual glycosides such as steviosides, rebaudioside-A, or mixtures thereof, and generally involve the use of organic chemical solvents (e.g., methanol and butanol) and synthetic adsorbents for extraction steps, selective recrystallization and purification. The use of such chemicals are not recommended by the global food industry and are not considered green or environmentally friendly. Moreover, even though the use of ethanol as an extraction solvent is permitted by the food industry, it has been proposed that ethanol extraction may change the taste profile of *stevia* extracts. Therefore, it is recommended that the *stevia* industry use non-ethanol extraction processes to avoid having taste issues.

Most of the research and development in the *stevia* industry is focused on developing extraction methods that yield a product with the highest possible sweetness and lowest possible bitterness. Of the various compounds present in *stevia* extracts, rebaudioside A is generally considered to exhibit the greatest utility as a sugar substitute. Thus, most of the *stevia* industry has developed complex methods involving sophisticated equipment in order to produce concentrations of rebaudioside A at 95% or higher, or to reach concentrations of at least 90%, but preferably 95%, for both stevioside and rebaudioside A combined.

Although *stevia* leaves have been predominantly studied for their sweetening properties, they are composed of, by dry weight: about 6.2% protein; about 5.6% lipids; about 52.8% total carbohydrates; about 15% steviosides and about 42% of water-soluble substances (Kinghorn et al., 1992). Additionally, *stevia* leaves are a significant source of potentially health benefiting phytochemicals. Over 100 *stevia*-derived phytochemicals have been discovered thus far. The constituents of *stevia* leaves can be divided into two categories: sweetening constituents and non-sweetening constituents.

The sweetening constituents represent about 14% by weight of dried leaves and are mostly diterpene glycosides based on the kaurene skeleton. In particular, steviol glycosides are responsible for the sweetening properties of *stevia*. The most abundant form of steviol glycosides in *stevia* leaves are steviosides followed next by rebaudiosides. The rest of the sweetening compounds are present in much smaller quantities. Stevioside was isolated in 1931 and has also been produced from the hydrolysis of stevioside as well as isosteviol (Bridel et al., 1931). Subsequent studies have led to the isolation of seven other sweet glycosides of steviol. Among these, rebaudioside A is considered the sweetest and the most stable, and it is less bitter than stevioside. Rebaudioside A represents a much smaller percentage of the total weight of *stevia* leaves and thus chemical processes aimed at producing higher yield of rebaudioside A (Reb A) have been developed (Dobberstein et al., 1986). Rebaudioside E (Reb E) is as sweet as stevioside, and rebaudioside D (Reb D) is as sweet as rebaudioside A, while the other glycosides are less sweet than stevioside (Crammer and Ikan, 1986; Crammer and Ikan, 1987). The sweetness of high potency sweeteners compared to sucrose are summarized in Table 1 (Crammer and Ikan, 1986).

TABLE 1

Sweetness of high potency sweeteners in Sucrose Equivalence (% SE) in water

| Sweetener | % SE |
| --- | --- |
| Aspartame | 16.0 |
| Acesulfame-K | 11.6 |
| Sucralose | 13.0 |
| Neotame | 15.1 |
| Cyclamate-Na | 15.2 |
| Saccharin-Na | 10.1 |

TABLE 1-continued

Sweetness of high potency sweeteners in
Sucrose Equivalence (% SE) in water

| Sweetener | % SE |
|---|---|
| JSSG | 10.1 |
| Rebaudioside D | 10.1 |
| Neohesperidin Didydrochalcone | 9.8 |
| Monoammonium Glycyrhisinate | 7.3 |

The sweetening potency of the different glycosides from *stevia* compared to sucrose. Stevioside is the most prevalent glycoside in *stevia*, comprising 6-18% of *stevia* leaves. Typical proportions, on a dry weight basis, for the four major glycosides found in the leaves of wild *stevia* plants are: 0.4-0.7% dulcoside A; 1-2% rebaudioside C; 2-4% rebaudioside A; and 5-10% stevioside (Wood et al., 1955). Table 2 summarizes the sweetness of the principal steviol glycosides found in *stevia* leaves compared to sucrose.

TABLE 2

Comparison of the sweetness potential of the principal steviol
glycosides found in *stevia* leaves (compared to sucrose).

| Steviol glycoside | Sweetness compared to sucrose |
|---|---|
| Dulcoside A | 50-120 fold |
| Rebaudioside A | 250-450 fold |
| Rebaudioside B | 300-350 fold |
| Rebaudioside C | 50-120 fold |
| Rebaudioside D | 240-450 fold |
| Rebaudioside E | 150-300 fold |
| Steviobioside | 100-125 fold |
| Stevioside | 300 fold |

The non-sweetening constituents of *stevia* leaves that have been identified include labdanediterpene, triterpenes, sterols, flavonoids, volatile oil constituents, pigments, gums and inorganic matter (Kinghorn et al., 1992). Table 3 summarizes the main non-sweetening constituents found in *stevia* leaves (Bridel et al., 1931).

TABLE 3

*Stevia*-derived molecules classified by chemical group and affinity

| | |
|---|---|
| Glycosylated diterpene derivatives | Steviol (ent-13-hydroxy kaur-16-en-19-oic acid) |
| | Stevioside |
| | Steviolbioside |
| | Rebaudioside A |
| | Rebaudioside B |
| | Rebaudioside C (Dulcoside B) |
| | Rebaudioside D |
| | Rebaudioside E |
| | Dulcoside A |
| Essential oils | β-caryophyllene |
| | Trans β-tarnesene |
| | α-humulene |
| | δ-cadiene |
| | caryophyllene oxide |
| | Nerolidol |
| | Linalol |
| | α-terpineol |
| | Terpinen-4-ol |
| Sterol derivatives | Stigmasterol |
| | β-sitosterol |
| | Campesterol |
| Flavonoids | Glucosyl-4'-O-apigenin |
| | Glucosyl-7-O-luteolin |
| | Rhamnosyl-3-O-kaempferol |
| | Quercetin |

TABLE 3-continued

*Stevia*-derived molecules classified by chemical group and affinity

| | |
|---|---|
| | Glucosyl-3-O-quercetin |
| | Arabinosyl-3-O-quercetin |
| | 5,7,3'-methoxyflavone |
| | 3,6,4'-methoxyflavone |

Methods for preparing *stevia* extracts are known in the art. In general, they involve the following steps: (1) extraction; (2) pre-treatment; (3) separation, and (4) refining. In some cases, *stevia* leaves are treated with non-polar solvents such as chloroform or hexane to remove essential oils, lipids, chlorophyll, and other non-polar substances. Methods for isolating sweetening compounds from dried *stevia* leaves usually involve a solid/liquid extraction step followed by a liquid/liquid purifying step. When this method is used, the glycosidic extract has a pronounced aftertaste which can be attributed to the presence of oils, tannins, and flavonoids (Phillips, 1987).

The extraction processes generally involve an initial liquid extraction using a solvent such as water, methanol, or a mixture of the two. Pressurized fluid extractions using water or methanol have been studied for the extraction of stevioside from *stevia* leaves. The results of these studies indicated that methanol has a better extraction ability than water within at temperatures between 110-180° C. (Pol et al., 2007). Supercritical fluid extractions with $CO_2$ and a co-solvent (e.g., methanol, ethanol, and acetone) have been suggested (Tan et al., 1988; Pasquel et al., 2000). It was claimed that the quality of the glycosidic fraction obtained thereby, in terms of its sweetening capacity, is higher in comparison with the one obtained with conventional methods in the art. Other groups have proposed using more complex microwave-assisted extraction (MAE) methods for isolating stevioside and rebaudioside A (Jaitak et al., 2009).

Besides the choice of solvent and the mode of extraction used, other parameters are known to affect the quality of the *stevia* extraction as well as the quantity of impurities (e.g., protein, pigments, pectin, and flavonoids) present therein. These parameters include pH and temperature. For example, it is known that the yield of sweetening compounds is usually higher when using higher extraction temperatures; however, this is known to lead to an undesirable crude extract which is of lower quality (containing a higher concentration of impurities such as undesirable bitter high molecular weight compounds). To counter this problem, the level of impurities can be reduced by precipitation with $CaCO_3$ at pH of 10. The use of ultrasonic waves during extraction has also been proposed to increase recovery (Shoji et al., 1999). Higher extraction temperatures can also lead to an increase in pigment impurity concentration. For example, a column-based extraction performed at 50° C. can lead to nearly double the concentration of pigment impurities in comparison with a column-based extraction performed at 25° C. Furthermore, an extraction temperature of 4° C. can reduce the quantity of impurities to about 70% of that of a corresponding extraction performed at 25° C. Thus, according to the teachings of the prior art, the level of pigments (and other undesirable such as bitter high molecular weight compounds) is higher when extracted at high temperatures (e.g., 25° C. to 50° C.) than at lower temperatures (e.g., 4° C.). Consequently, the prior art teaches that a *stevia* extract is of better quality when extracted at low temperatures.

While water-based extraction methods for *stevia* have been previously described, these methods tend to be rather complicated, less or not efficient, costly and require the use of organic chemical solvents. A water-based *stevia* extraction method that qualifies as "organic certifiable" and which does not require the addition of other solvents or chemicals, has yet to be developed.

A variety of pre-treatment strategies have also been employed in the *stevia* industry to enhance the efficiency of the extraction process. However, these additional strategies necessitate an additional step to the extraction process, and therefore can increase the cost and time of the extraction and/or require the use of complex apparatuses. For example, the use of inorganic salts such as $Ca(OH)_2$ is commonly used. Other inorganic salts that are sometimes used include sulfates of potassium, aluminum, and iron (Fuh et al., 1990; Adduci et al., 1987; Yokoyama and Sugiyama, 1990). Aluminum salts have been used to remove pigment from the crude extract. Heat evaporation processes have been also used. Ceramic microfiltration provides chemical-free pre-treatment to remove large suspended impurities from the crude extract. Membrane separation technology can substitute a heat-evaporation process. Ultrafiltration is the most common method for separation of remaining larger molecular weight impurities from the clarified extract (Kutowy et al., 1998; Fuh et al., 1990. Liu et al., 1991).

Purification steps involving ion exchange and adsorption column chromatography have been used for isolating sweeteners. However once again, these techniques are often complex (e.g., requiring numerous steps), time-consuming, costly, directed to the separation of individual glycosides, and/or often involve the use of organic chemical solvents and/or other synthetic chemicals which are not recommended by the food industry. Briefly, the use of strongly acidic cation-exchange resin, strongly basic exchange resin, as well as mixed bed columns of weakly acidic cation-exchange resin and weakly basic anion-exchange resin have been used in complex processes to isolate stevioside with a purity of 80-87% and a recovery of about 79% (Cheng and Chang, 1985). Furthermore, a bifunctional polymeric adsorbent was stated to achieve higher recovery for rebaudioside A than the commercial resin with stable and easier regeneration capacity (Shi et al., 2002). In other studies, active carbon has also been used for the adsorption of stevioside, in which an optimal ethanol concentration for stevioside desorption was reported to be 60-65%. A significantly higher amount of rebaudioside A was recovered with active carbon from an aqueous solution (Chang et al., 1980). Nanofiltration has been used to refine and concentrate the permeate following an ultrafiltration step. In this regard, a higher temperature nanofiltration was shown to remove certain low molecular weight compounds that might contribute to the bitter taste of the final product (Kutowy et al., 1998). Flavonoids such as apigenin-4'-o-glucoside, quercitrin, and others were shown to be present in water-based *stevia* extracts (Rajbhandari et al., 1979). These flavanoids are yellowish in color, have a bitter taste, and are of lower molecular weight than *stevia* glycosides, allowing them to permeate through the nanofiltration membranes. Subsequent purification steps are generally employed to improve yield and/or purity involving an additional extraction in polar organic chemical solvent, decoloration (removal of colored pigments), coagulation, ion exchange chromatography and crystallization (Pasquel et al., 2000; Kinghorn et al., 1985). The filtrate can then be re-precipitated and re-filtered to yield a 90% pure stevioside extract (Adduci et al., 1987; Yokoyama et al., 1990). Thus, many complex and/or costly techniques have been previously employed or are still used in the purification of *stevia*.

Commercially available *stevia* extracts contain a high percentage of the glycoside diterpenes stevioside (CAS no. 57817-89-7) and rebaudioside A (CAS no. 58543-16-1), the principal sweetening compounds, and smaller amounts of other steviol glycosides. The exact composition of the extracts depends on the composition of the *stevia* leaves from which they originate, which in turn are influenced by factors such as soil, climate, cultivation methods, harvest time, as well as on manufacturing process including the extraction and purification methods used. The impurities present in *stevia* extracts are primarily due to other compounds that are co-extracted from *stevia* leaves, such as pigments and saccharides. Regulatory submissions from countries in different parts of the world suggest that the main components of commercially available extracts of *stevia* contain, as the main components, stevioside and rebaudioside A. The amounts of these compounds range from about 10-70% for stevioside and about 20-70% for rebaudioside A. Furthermore, most commercially available *stevia* extracts have a total steviol glycoside content of more than 90%, with the two main steviol glycosides (stevioside and rebaudioside A) making up about 80% of the extracts (Wallin, 2004).

According to Phillips et al., (1987) the bitter aftertaste in *stevia* extracts is due to the presence of essential oils, tannins, and flavonoids. However. Soejarto et al., (1983) concluded that the sesquiterpene lactones are responsible for the bitter aftertaste, while Tsanava et al., (1991) suggested that caryophyllene and spathulenol contribute decisively to the aftertaste. Nevertheless, along with providing sweetness, it appears that at least a portion of the aftertaste is attributable to stevioside and rebaudioside A, although the contribution of rebaudioside A is significantly less than that of stevioside (Jakinovich et al., 1990).

Different methods exist for improving the taste of *stevia* extracts (e.g., diminishing its bitter aftertaste). The methods involve enzymatic modification of stevioside by pullanase, isomaltase (Lobov et al., 1991), β-galactosidase (Kitahata et al., 1989), or dextrin saccharase (Ghanta et al., 2007). Another method involves adding thaumatin, a natural protein that is a low calorie flavor modifier, which is extracted from the fruits of the katemfe (*thaumatococcus daniellii*) tree from the West African rain forest. Yet another method suggests enriching the extract with rebaudioside A and rebaudioside D. Furthermore, exposure to low pH (acidic conditions including citric acetic and malic tartaric acid) have been reported to enhance the sweetness of *stevia* extracts. Finally, the addition of plant (Ogawa) extracts which are natural *stevia* optimizers, have the ability to mask the unpleasant aftertaste of *stevia*.

Thus, there remains a need for a method for preparing an organic certifiable *stevia* extract with high sweetness which is less complex, less costly, less expensive, less time consuming, environmentally friendly and does not employ organic chemical solvents which may be unfit for human consumption, and would otherwise qualify for "organic certification" yet is amenable to large-scale production. The present invention seeks to address these and other needs.

The present description refers to a number of documents, the content of which is herein incorporated by reference in their entirety.

SUMMARY OF THE INVENTION

In one embodiment, the invention relates to a simple extraction method for preparing an organic certifiable *stevia* extract with high sweetness and optionally with enhanced antioxidant properties. A number of advantages are associated with the extraction method of the present invention compared to other existing extraction methods employed by the *stevia* industry. These latter methods tend to be rather complex (often requiring many steps), expensive, time consuming, not environmentally friendly, employ organic chemical solvents which may be unfit for human consumption, and require their removal. Furthermore, the use of these solvents, among other things, precludes the *stevia* extracts from receiving an "organic certification" from regulatory bodies. In contrast, the extraction method of the present invention is simple (i.e., minimal sophisticated equipment is required), cost-effective, relatively rapid and less complex (i.e., requiring less steps compared to methods employed in the *stevia* industry). Furthermore, it does not employ the use of organic chemical solvents that are unfit for human consumption, thereby allowing it to qualify for "organic certification".

Other aspects enable the *stevia* products and extraction methods of the present invention to qualify for "organic certification" include at least one of: (1) the fact that the seeds used to grow the *stevia* plants are certified organic; (2) the *stevia* plants are grown under organic conditions; and (3) no chemicals are used during the extraction except for solvents generally recognized as safe (GRAS) (e.g., water and ethanol).

In one embodiment, a further advantage of the extraction method of the present invention is its ability to be easily adapted for large-scale production.

In yet another embodiment, the invention relates to an organic certifiable *stevia* extract with high sweetness. In a related embodiment, the invention relates to such as extract having enhanced antioxidant properties.

In yet another embodiment, the extraction method of the present invention involves a hot water-based extraction of *stevia* leaves that have been dried and grinded (e.g., crushed or powdered), allowing the dissolution of the sweetening compounds naturally present therein. These sweetening compounds include steviosides and rebaudioside A, which are purified from the water-based extracts (i.e., the crude extraction solution) by two or more successive chromatographic or equivalent purifications steps. By "equivalent purification steps", it is meant contacting the crude extraction solution with at least a first resin which removes unwanted pigments and at least a second resin which retains the desired sweetening compounds. The sweetening compounds are then eluted from the second resin with an appropriate elution solution (e.g., ethanol).

In one aspect, the present invention provides a method for preparing a *stevia* extract having high sweetness, said method comprising:
 (a) extracting sweetening compounds from a dried and grinded preparation of *stevia* leaves by contacting same with at least a first hot extraction solvent being generally recognized as safe (GRAS) to form a crude extraction solution;
 (b) removing pigments from said crude extraction solution by contacting same with a strongly basic anion exchange resin;
 (c) isolating said sweetening compounds by contacting the depigmented crude extraction solution of (b) with a hydrophobic or non-polar resin; and
 (d) eluting the sweetening compounds isolated from (c) by contacting said hydrophobic or non-polar resin with an elution solvent being GRAS,
thereby producing said *stevia* extract having said high sweetness.

In one embodiment, the ratio of the above mentioned preparation of *stevia* leaves to the above mentioned first hot extraction solvent is about 7% to about 14% in terms of weight to volume. In another embodiment, the above method further comprises extracting the preparation of *stevia* leaves following (a) with a second hot extraction solvent being GRAS to form additional crude extraction solution. In another embodiment, the second hot extraction solvent is the same as the first hot extraction solvent. In another embodiment, the second hot extraction solvent has a temperature lower than that of the first hot extraction solvent. In another embodiment, the hot extraction solvent has a temperature of about 50° C. to about 100° C., about 60° C. to about 95° C., or about 80° C. to about 85° C. In another embodiment, the above extraction is performed for about 15 minutes to about 60 minutes.

In another embodiment, the above hot extraction solvent is water or ethanol. In another embodiment, the above elution solvent is ethanol. In another embodiment, the ethanol is grape ethanol. In another embodiment, the concentration of the ethanol is about 60% to about 94%. In another embodiment, the concentration of the ethanol is about 80%.

In yet another embodiment, the method of the invention further comprise step a') performing an electrocoagulation of the solution resulting from step a) for clarifying the solution and eliminating undesirable substances (e.g. contaminants) prior to step by In another embodiment, the above strongly basic anion exchange resin in (b) is an IRA-900 resin. In another embodiment, the above hydrophobic or non-polar resin of (c) is a polymeric adsorbent resin, a crosslinked polystyrene copolymer resin, or an XAD-2 resin. The skilled person would clearly understand the scope of the term "non-polar", as well as the kinds of compounds that it encompasses.

In another aspect, the present invention provides a method for preparing a *stevia* crude extraction solution having high sweetness and antioxidant activity, the method comprising extracting sweetening compounds from a dried and grinded preparation of *stevia* leaves by contacting same with at least a first hot extraction solvent being GRAS to form the crude extraction solution having high sweetness and antioxidant activity. In one embodiment, the method further comprises an extraction with at least a second hot extraction solvent being GRAS. In another embodiment, the first hot extraction solvent is water. In another embodiment, the second hot extraction solvent is ethanol.

In another aspect, the present invention provides a *stevia* extract with high sweetness having a purity of sweetening compounds of at least 90%. In another embodiment, the *stevia* has a purity of sweetening compounds of at least 95%.

In another aspect, the present invention provides a *stevia* extract produced by any one of the above mentioned methods. In one embodiment, the *stevia* extract of the present invention is organic certifiable. In another aspect, the present invention provides a composition comprising the *stevia* extract of the present invention and a pharmaceutically or neutraceutically acceptable carrier. In another aspect, the present invention provides a food product, food supplement, food additive or nutraceutical comprising the *stevia* extract of the present invention.

In another aspect, the present invention provides a method of treating a disease associated with oxidative stress comprising administering to a patient having the disease an antioxidant composition comprising the *stevia* of the present invention.

In another aspect, the present invention provides an organic certifiable *stevia* extract having high sweetness. In another aspect, the present invention provides an organic certifiable *stevia* extract having high sweetness and antioxidant properties.

Other objects, advantages and features of the present invention will become more apparent upon reading of the following non-restrictive description of specific embodiments thereof, given by way of example only with reference to the accompanying drawings.

DETAILED DESCRIPTION OF THE INVENTION

DESCRIPTION OF ILLUSTRATIVE EMBODIMENTS

Definitions

Figures 1A, 1B:
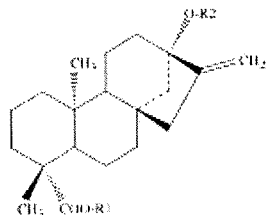
FIG. 1 is a representation of structures of (A) stevioside and (B) related compounds. In rebaudioside D and E, R1 is composed of 2β-Glc-β-Glc(2→1). Rebaudioside A, B, C, D, E and F comprise an additional R2 sugar moiety on carbon 3 of the first β-Glc. Rebaudioside F has one β-Glc substituted by -β-Xyl. Glc and Rha corresponding, respectively, to glucose and rhamnose sugar moieties (Wallin, 2004).
Figure 2:
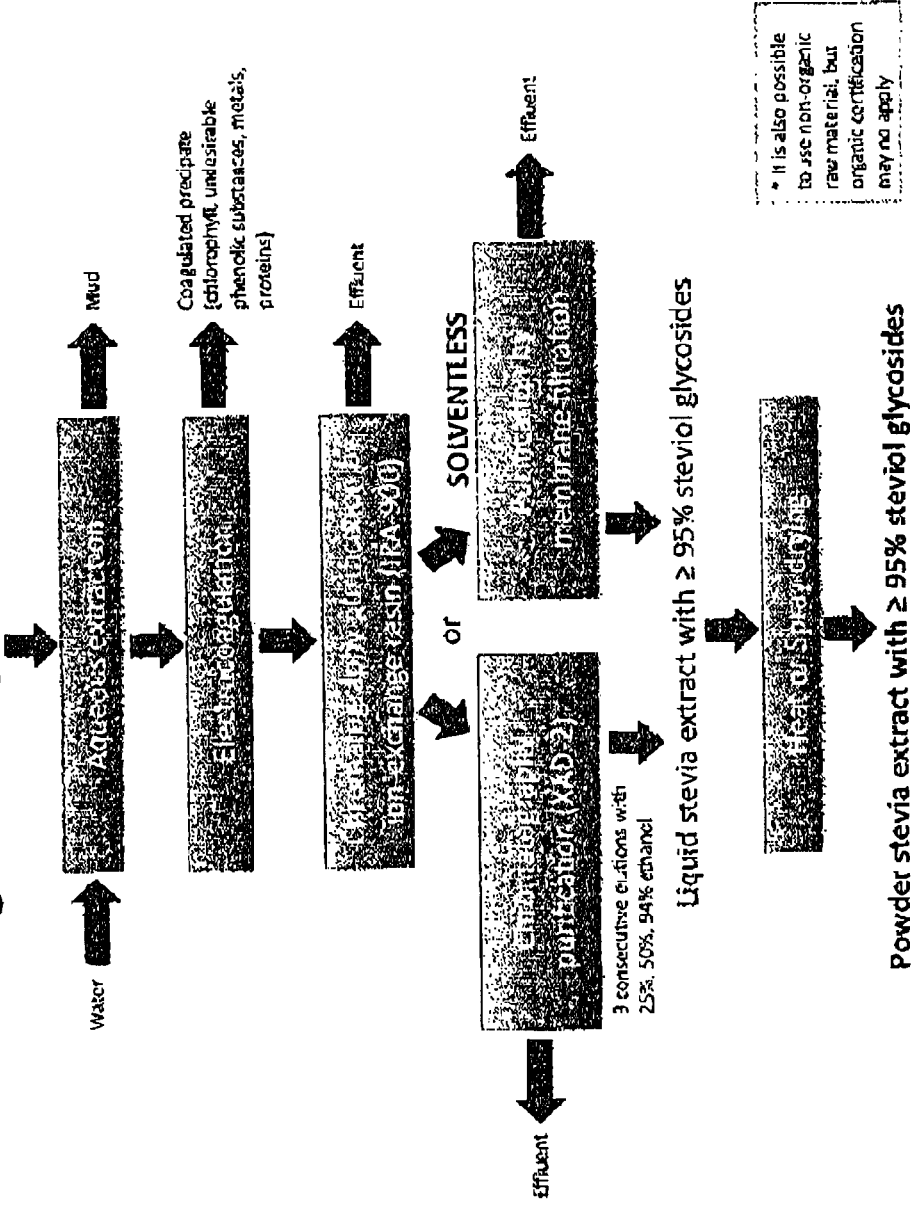
FIG. 2 shows a scheme outlining an example of the simplified extraction method of the present invention to obtain an organic *stevia* extract containing at least 95% steviol glycosides obtained using ethanol or non-ethanol process.
Figure 3:
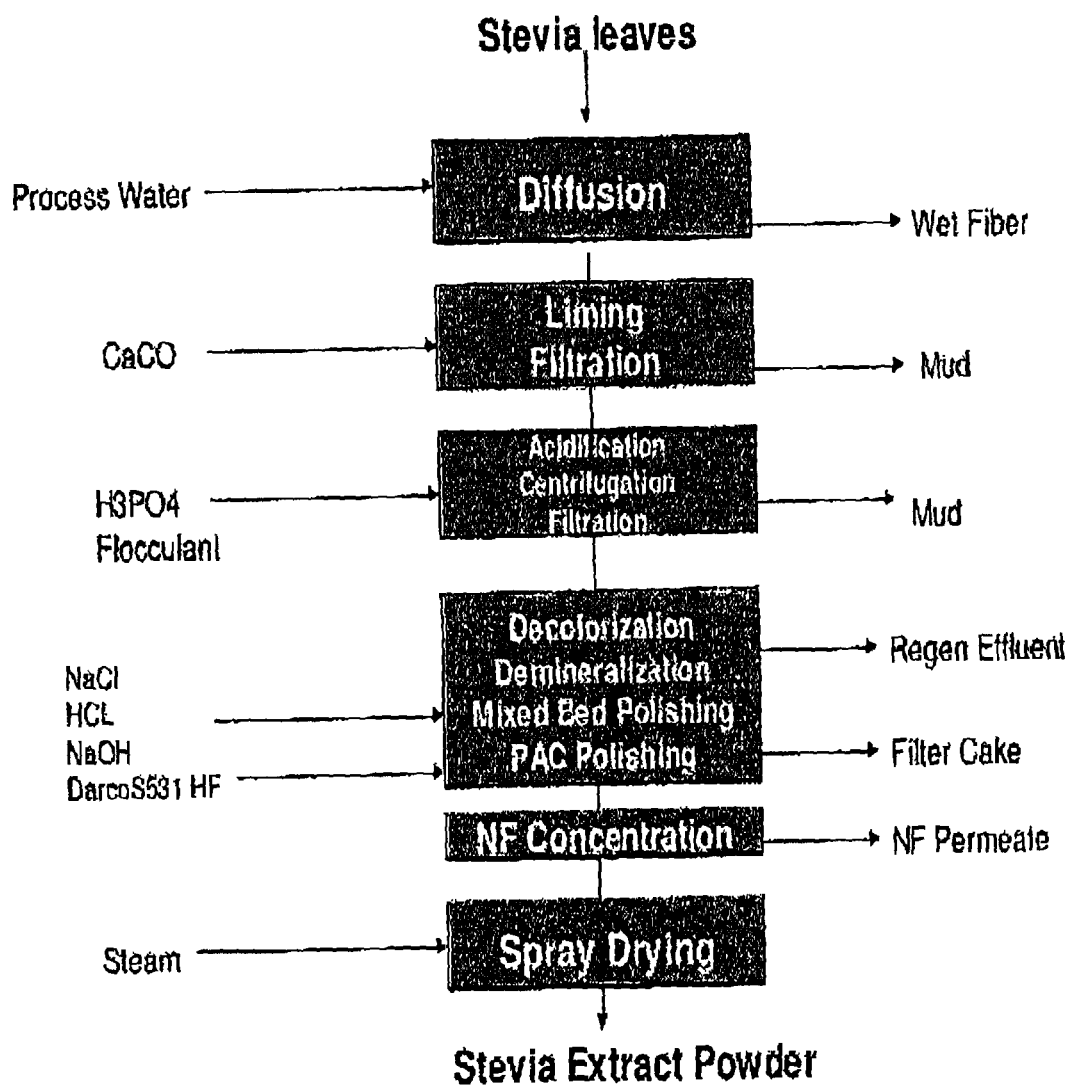
FIG. 3 is an example of a typical extraction method employed in the *stevia* industry to obtain a 95% pure rebaudioside A extract powder (prior art).

In the present description, a number of terms are extensively utilized. In order to provide a clear and consistent understanding of the specification and claims, including the scope to be given such terms, the following definitions are provided.

The use of the word "a" or "an" when used alone or in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The term "subject" or "patient" as used herein refers to an animal, preferably a mammal, and most preferably a human who is the object of treatment, observation or experiment.

"Mammal" includes humans and both domestic animals such as laboratory animals and household pets, (e.g. cats, dogs, swine, cattle, sheep, goats, horses, rabbits), and non-domestic animals such as wildlife and the like.

As used herein, the term "purified" refers to a compound (e.g., steviosides, rebaudioside A, quercetin and the like) having been separated from a component of the composition in which it was originally present. The term purified can sometimes be used interchangeably with the term "isolated". Thus, for example, "purified or isolated quercetin" has been purified to a level not found in nature. A "substantially pure" compound or molecule is a compound or molecule that is lacking in most other components (e.g., 30, 40, 50, 60, 70, 75, 80, 85, 90, 95, 96, 97, 98, 99, 100% free of contaminants). By opposition, the term "crude" means compounds or molecules that have not been separated from the components of the original composition in which it was present. Therefore, the terms "separating", "purifying" or "isolating" refers to methods by which one or more components of the biological sample are removed from one or more other components of the sample. A separating or purifying step preferably removes at least about 70% (e.g., 70, 75, 80, 85, 90, 95, 96, 97, 98, 99, 100%), more preferably at least about 90% (e.g., 90, 91, 92, 93, 94, 95, 96, 97, 98, 99, 100%) and, even more preferably, at least about 95% (e.g., 95, 96, 97, 98, 99, 100%) of the other components present in the sample from the desired component. For the sake of brevity, the units (e.g., 66, 67 . . . 81, 82, . . . 91, 92% . . . ) have not systematically been recited but are considered, nevertheless, within the scope of the present invention.

The compounds and extracts described herein can be formulated as pharmaceutical compositions by formulation with additives such as pharmaceutically acceptable excipients, pharmaceutically acceptable carriers, and pharmaceutically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles. As used herein, the term "pharmaceutically acceptable" refers to molecular entities and compositions that are physiologically tolerable and do not typically produce an allergic or similar unwanted reaction, such as gastric upset, dizziness and the like, when administered to human. Preferably, as used herein, the term "pharmaceutically acceptable" means approved by regulatory agency of the federal or state government or listed in the U.S. Pharmacopeia or other generally recognized pharmacopeia for use in animals, and more particularly in humans. The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The compounds, compositions and extracts of the present invention can be prepared as nutritional formulations such as foods, including medical or functional foods and dietary supplements. A "medical or functional food" is defined as being consumed as part of a usual diet but which has been demonstrated to have physiological benefits and/or to reduce the risk of a disease or condition such as a chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into foodstuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration and aim of the particular formulation can vary based on the individual subject, the stage of the disease or condition, and other factors evident to one skilled in the art. In the case of a pharmaceutical formulation as well as a nutraceutical formulation, during the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease or condition. Thus, a nutraceutical is a product isolated or purified from foods that is generally sold in medicinal forms not usually associated with foods. A nutraceutical is demonstrated to have a physiological benefit or provide protection against chronic disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically acceptable excipients may include liquid solutions such as a solution comprising a vegetable- and/or animal-and/or fish-derived oil.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds, compositions and extracts of the present invention may be administered as either a food or a food supplement. For example, when provided as a food, the extracts of the present invention are combined with material primarily made up of protein, carbohydrate and/or fat that is used in the body, preferably a human body, to sustain growth, repair, and vital processes, and to furnish energy. When provided as a food supplement, the compositions comprise selected substances such that they can be eaten at or about the same time as a food. The food supplements are generally eaten within about one hour before or after the food is eaten, typically within about one-half hour before or after the food is eaten, preferably within about 15 minutes of when the food is eaten, and further preferably within one to five minutes of the time the food is eaten. The food supplement can also be eaten at the same time as the food, or even with the food.

As used herein, the term "*stevia*" refers to the plant *stevia rebaudiana*, commonly known as sweetleaf, sweet leaf, sugarleaf, or simply *stevia* unless otherwise indicated. The phrase "*stevia* extract" refers to a sweetener-rich extract derived from the leaves of the *stevia rebaudiana* plant.

"Sweetness" refers to the measure of how sweet a substance is when tasted. Sucrose (i.e., table sugar) is the prototypical example of a sweet substance and is generally the reference point used to measure sweetness, for example, in terms of percentage sucrose equivalence or in terms of a fold increase in sweetness compared to sucrose. As used herein, the term "high sweetness" refers to a fold increase of at least 250 as compared to that of sucrose. In one embodiment, the present invention provides a *stevia* extract with a fold increase in sweetness of at least 250 as compared to that of sucrose. In another embodiment, the present invention provides a *stevia* extract with a fold increase in sweetness of at least 300 as compared to that of sucrose. In yet another embodiment, the present invention provides a *stevia* extract with a fold increase in sweetness of about 250 to about 400 as compared to that of sucrose.

As used herein, the phrase "hot water" in the context of an extraction solvent refers generally to water having a temperature of 50° C. to 100° C.

A "natural product" refers to naturally-occurring compounds that are end products of secondary metabolism; often, they are unique compounds for particular organisms or classes of organisms. An "all-natural product" refers to a product made with and/or from only natural compounds or products.

"Organic certification", "organic certifiable" or the like refers to a certification process for producers of organic food and other organic agricultural products. In general, any business directly involved in food production can be certified, including seed suppliers, farmers, food processors, retailers and restaurants. Requirements vary from country to country, and generally involve a set of production standards for growing, storage, processing, packaging and shipping that include, for example: avoidance of most synthetic chemical inputs (e.g. fertilizer, pesticides, antibiotics, food additives), genetically modified organisms, irradiation, and the use of sewage sludge; use of farmland that has been free from synthetic chemicals for a number of years (often, three or more); keeping detailed written production and sales records (audit trail);

maintaining strict physical separation of organic products from non-certified products; and undergoing periodic on-site inspections. In some countries, certification is overseen by the government, and commercial use of the term organic is legally restricted.

An "organic food" refers to a food made with ingredients derived from crops obtained from organic farming and made in a way that limits or excludes the use of synthetic materials during production. Organic agricultural methods are internationally regulated and legally enforced based in large part on the standards set by the International Federation of Organic Agriculture Movements (IFOAM). For greater clarity, unless otherwise specified the use herein of the term "organic" preceding any plant, animal or food product thereof refers to a product made with ingredients derived from crops obtained from organic farming and made in a way that limits or excludes the use of synthetic materials during production. For example, "organic *stevia*" refers to a *stevia* plant or extract thereof derived from organic farming or organic-certifiable production methods.

"Generally recognized as safe" or "GRAS" refers to an American Food and Drug Administration (FDA) designation that a chemical or substance added to food is considered safe by experts, and may be exempted from some other regulatory requirements. As used herein, a "biosolvent" is a solvent obtained from biological or organic sources. In one embodiment, the present invention utilizes a GRAS solvent. In another embodiment, the present invention utilizes a GRAS biosolvent. Examples of GRAS solvents or biosolvents included within the scope of the present invention are ethanol, sorbitol and mannitol. An example of a solvent or biosolvent not present on the FDA GRAS list is methanol.

As used herein, an "organic certifiable solvent" refers to a solvent that is permitted for use by organic certification agencies without, by itself, voiding organic certification. Currently, two solvents that satisfy this criteria are water and ethanol (preferably derived from organic plants). The phrase "organic certifiable solvent" as used herein should not be confused with the phrase "organic chemical solvent". The latter relates to the field of organic chemistry and refers herein to any solvent containing at least one carbon atom that does not include an "organic certifiable solvent" as defined above. For example, according to the present invention, ethanol (especially derived from organic plants) is considered an "organic certifiable solvent" but is not comprised within the definition of "organic chemical solvent". In contrast, according to the present invention, methanol is considered an "organic chemical solvent" but not an "organic certifiable solvent".

As used herein, an "organic certifiable *stevia* extract" refers to an extract from *stevia rebaudiana* obtained without the use of an organic chemical solvent as defined above, or of any other substance which would otherwise void organic certification. In one embodiment, the present invention relates to such an organic certifiable *stevia* extract. In another embodiment, the levels of purity of extracts of the present invention defined or referred to elsewhere, when more specifically relating to the methods of the instant application, also apply to the organic certifiable *stevia* extract as defined here.

As used herein, the phrase "sweetening compounds", "sweetener compounds", "sweetener" or the like generally refers to an additive (artificial or natural) which increases the basic taste of sweetness of a product to be ingested and can be considered as a sugar substitute (with or without additional calories). In one embodiment, these phrases refer to the sweetness-enhancing compounds from *stevia*, including glycosides, steviosides and rebaudiosides. Furthermore, *stevia* is the only known natural sweetener with zero calorie.

"Antioxidant compounds" refers to any molecules capable of slowing or preventing the oxidation of other molecules that may cause oxidative stress and may damage or kill cells. Oxidative stress is thought to be associated with many human diseases. In one embodiment, an antioxidant compound of the present invention is quercetin.

A "food additive" refers to any substance added to foods during processing thereof to improve characteristics such as color, texture, flavor, and/or conservation. A "food supplement", "dietary supplement" or "nutritional supplement", refers to a preparation intended to provide nutrients, such as vitamins, minerals, fiber, fatty acids or amino acids, that may be missing or may not consumed in sufficient quantities in an individual's diet.

"Medical food" refers to any food that is specially formulated and intended for the dietary management of a disease that has distinctive nutritional needs that cannot be met by normal diet alone.

A "functional food" is similar in appearance to, or may be, a conventional food that is consumed as part of a usual diet, and is demonstrated to have physiological benefits and/or reduce the risk of chronic disease beyond basic nutritional functions, i.e. they contain a bioactive compound.

Harvesting and Processing of *Stevia* Leaves

The harvested raw material for extraction (i.e., *stevia* leaves) is dried and grinded. Drying of the *stevia* leaves can be done under the sun or via other drying methods. In one embodiment, drying of the *stevia* leaves involves the application of heat. In another embodiment, the drying process involved exposing the leaves to a temperature of between 25° C. and 50° C. In another embodiment, the *stevia* leaves are crushed or grinded (e.g., manually or with the aid of a machine) into a powder. Other techniques for drying and grinding *stevia* leaves would be within the grasp of the skilled person. Grinding of the raw material raises the extraction yield but may also increase the level of impurities while also potentially making filtration more difficult. Consequently, the skilled person will adapt this grinding step in accordance with the final method used and the desired levels of purity.

Extraction of Grinded and Dried *Stevia* Leaves with GRAS Solvent

Following harvesting and processing, the grinded and dried *stevia* leaves are extracted with an appropriate GRAS solvent of the present invention. According to the present invention, a number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material:solvent) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results.

In one embodiment, a GRAS solvent is used for the extraction described herein. In one embodiment, the GRAS solvent is water. In another embodiment, the GRAS solvent is ethanol, preferably obtained from natural organic sources (e.g., grape alcohol). In yet another embodiment, the solvent comprises a mixture of water and ethanol.

The temperature and time at which the chosen GRAS solvent is used can affect the overall yield, quality and/or purity of the extract. In general, an extraction solvent used at a higher temperature increases, for example, the solubility of the compounds of interest that are to be extracted. According to the present invention, an increase in temperature of the solvent may also increase the yield of certain compounds of interest by, for example, inactivating the enzyme polyphenoloxydase (PPO), which is known to oxidize polyphenols in plants. Thus, in one embodiment, the solvent of the present invention is hot water having a temperature of about 80° C. or about 85° C. In another embodiment, the solvent of the present invention is hot water having a temperature of between about 50° C. and about 100° C. In another embodiment, the solvent of the present invention is hot water having a temperature of between any one of about 55° C., 60° C., 65° C., 70° C., 75° C. and 80° C., and any one of about 85° C., 90° C., 95° C. and 100° C. Other temperature ranges falling within about 50° C. and about 100° C., which are not specifically recited here for brevity, are nevertheless included within the present invention and considered herein as being "hot". Furthermore, different combinations of the above temperatures and GRAS solvents used in successive extractions are included within the scope of the present invention. For example, a first hot water extraction can be performed at about 85° C. and, following a filtration step, a second hot water extraction can be performed at about 60° C., resulting in a high extraction yield of sweetening compounds (e.g., 96%). Furthermore, the above extractions can be conducted for a period of time (e.g., an incubation period) which enables the desired level of dissolution of the compounds of interest. In one embodiment, this period of time can vary depending on other conditions, for example, the temperature of the solvent that is used and the length of the incubation period. It would be within the grasp of the skilled person to adapt the dissolution time to suit their particular needs and to reach an acceptable level of dissolution of the compounds of interest. In one embodiment, the above extractions can be performed for about 15 minutes to about 60 minutes. In another embodiment, the above extraction can be performed for about 15, 16, 17, 18, 19, 20, 21, 22, 23, . . . 60 minutes. For brevity, all the dissolution times encompassed by the present invention have not been specifically recited here but are nevertheless included.

The percentage (ratio or concentration) of raw material to solvent (raw material:solvent or raw material/solvent) should be considered as it can also significantly affect the yield obtained by the extraction method. According to the present invention, the choice of ratio or percentage of raw material to solvent can be chosen to, for example, increase the relative yield (i.e., the total amount of compounds of interest obtained following the extraction per amount of starting raw material) or to increase productivity (i.e., the total amount of the compounds of interest obtained following the extraction for each purification). For example, a ratio or percentage can be chosen to maximize relative yield, which also minimizes loss or waste of the compounds of interest. Alternatively, a ratio or percentage can be chosen to maximize productivity, in which case a higher amount of the compounds of interest can be obtained for each purification at the expense of higher relative loss or waste. Based on the teachings of the present invention, the skilled person would be able to adapt the percentage of raw material to solvent to suit their particular needs (e.g., market conditions). For example, if the cost of raw material (e.g., *stevia* leaves) was low, one may wish to use a higher percentage of raw material to solvent in order to maximize productivity. On the other hand, if the cost of raw material was high, then a lower percentage of raw material to solvent can be chosen in order to maximize relative yield and minimize waste. The skilled person would understand that, even though the percentage of raw material to solvent may be kept constant, the absolute amounts of raw material and solvent that are used can also affect the yield of the compounds of interest. For example, the yield obtained from larger volumes (and greater amounts of starting material) may differ from the yield obtained from a smaller volume depending on factors such as the specifications of the extraction equipment employed. Addressing such types of scale-up issues would be within the grasp of the skilled person.

In one embodiment, the percentage of raw material to solvent (mass/volume) is such that it allows sufficient extraction of the sweetening compounds of the present invention, for example, in terms of yield and purity. In another embodiment, the percentage of raw material to solvent (mass/volume) is between about 7% and about 14%. In another embodiment, the percentage of raw material to solvent is about 7%, about 12% or about 14%. In another embodiment, the percentage of raw material to solvent is 7, 8, 9, 10, 11, 12, 13, or 14%.

The number of successive extractions performed can also impact the extraction yield. In general, a higher yield can be obtained by increasing the number of successive extractions. For example, two successive extractions (i.e., a double extraction) may increase the yield of sweetening compounds (e.g., steviosides and rebaudioside A) by 25-30% compared to a single extraction. In one embodiment, the extraction method of the present invention involves one extraction. In another embodiment, the extraction method of the present invention involves two or more extractions, which includes but is not limited to at least 2, 3, 4, 5, 6, 7, 8, 9 or 10 successive extractions. For brevity, other values greater than those listed have not been explicitly recited here but are nevertheless included. The skilled person would understand that while increasing the number of successive extractions increases the yield of final product, performing an excessive number of successive extractions may not be practical, and may lower the concentration of the desired products below desirable levels.

In one embodiment, multiple successive extractions using combinations of different solvents can be performed. In another embodiment, a first extraction can be performed with hot water and a second extraction can be performed with hot ethanol. In another embodiment, a first extraction can be performed with hot ethanol and a second extraction can be performed with hot water. In accordance with the present invention, the skilled person will understand that the use of multiple successive extractions using combinations of different solvents can increase the yield of sweetening compounds in the crude extraction solution. In this regard, the skilled person will be able to adapt the choice of solvents, as well as their order or use, in order to obtain the desired levels of sweetening compounds in the final product.

A step of separating the grinded raw material from the solvent can be performed between the successive extractions. For example, the separation between the extracts and the grinded raw material can be achieved by filtration with or without vacuum. A variety of filtration means can be used to accomplish this separation, In one embodiment, filtration is accomplished by the use of a cellulose filter (e.g., cellulose paper), for example, having a pore size of 5 μm. In another embodiment, the filtration means is a polypropylene filter. Other suitable filtration means commonly used in the *stevia* industry would be within the grasp of the skilled person. In one embodiment, the raw material can be pressed following separation to maximize the yield of the extraction.

Electrocoagulation

Electrocoagulation is an electrochemical technique that consist in the in situ generation of cations, particularly aluminum ions ($Al^{+3}$) that form a gel of cationic hydroxide with $OH^-$ ions, particularly aluminum hydroxide $Al(OH)_3$, at optimal values of pH. The aluminum hydroxide thus formed will provoke the coagulation by coprecipitation and adsorption of several undesirable substances present in the treated solution. Such undesirable substances may be, for example, chlorophyll, phenolic substances, metals, proteins etc.

Principle of the Method

Electrocoagulation is based on the principle of soluble anodes. An electric current is generated between two electrodes of aluminum immersed in the solution (i.e. liquid extract) to be treated. The solution provides the electrolytes of which conductivity is increased by the addition of sodium chloride at a concentration of 0.1% w/v.

An oxydoreduction reaction is carried out:

Anode:
$Al \rightarrow Al^{3+} + 3e^-$ (oxidation of the sacrifical anode)

Cathode:

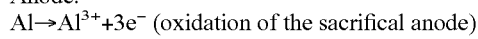

$2 H_2O + 2e^- \longrightarrow 2 OH^- + H_2^-\uparrow$ (decomposition of solvent)

The center solution is constantly agitated, $Al^{+3}$ ions formed at the anode are brought into solution and react with $OH^-$ ions to form aluminum hydroxide. The reactor's and electrodes' geometry, current power and time of electrolysis are all determined in function of the volume of solution to be treated. It is possible to determine the quantity of aluminum produced from the following relation:

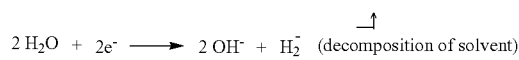

$$m = \frac{I \times t \times M}{nF}$$

wherein
m=mass of metal dissolved in grams (g)
I=intensity of current imposed in ampere (A)
t=duration of electrolysis in second (s)
M=Molecular weight of aluminum in g.mol$^{-1}$
F=Constant of Faraday (69500 C mol-1)
N=number of electrons put in play in the reaction Electrocoagulation is more efficient than classical solvent extraction method in removing plant pigments, while not affecting the important secondary metabolites (Jumpatong et al, 2006). Electrocoagulation has been used to remove chlorophyll, undersirable phenolic compounds such as tannins, and proteins from plant based-technology (Robic and Miranda, Jumpatong et al, 2006). Electro-Pure Systems, Inc. conducted a Superfund Innovative Technology Evaluation (SITE) demonstration in the early 1990s using alternating current electrocoagulation (ACE) (Barkley, Farrell, and Williams 1993). The ACE project demonstrated variable metal removal efficiencies as operating parameters changed. Removal rates were reported at 66%-96% for lead, 90%-100% for copper, 87%-94% for chromium, and 14%-99% for cadmium. The lower removal percentages were seen when treating water containing high concentrations of metals (Barkley. Farrell, and Williams 1993). Jumpatong K. Phutdhawong W, Buddhasukh D. 2006. Dechlorophyllation by electrocoagulation. Molecules 11:156-162. Robic G and Everson Alves Miranda. Electrocoagulation as a clarification in plant-based bioprocesses. Barkley, N. P., C. Farrell, and T. Williams. 1993. *Electro-Pure Alternating Current Electrocoagulation: Emerging Technology Summary*. EPA/540/S-93/504

Purification of the Compounds of Interest

A number of purification means can be employed to purify the compounds of interest from a *stevia* extract, including sweetening compounds such as stevioside and rebaudioside A. According to the present invention, separate purification methods can be employed to, for example, maximize the yield and/or purity of either the sweetening compounds.

To purify sweetening compounds of interest, two purification means can be used in succession. For example, chromatographic purification using different gel columns in succession can be employed. The first column can be an anionic exchange column used in order to remove non-sweetening components such as chlorophyll and flavonoids. In this case, the sweetening compounds of interest (e.g., rebaudioside A and stevioside) are not retained in the column and flowthrough. In a subsequent step, a second means of purification is used (e.g., a reverse phase column) to absorb and retain the rebaudioside A and stevioside allowing further non-sweetening component to flow through and be removed. The skilled person will recognize that the first and second means of purification can each be repeated subsequently one or more times on the same sample in order to remove an even higher amount of pigments or other impurities to obtain a final product of even higher purify. In this regard, the skilled person will be able to adapt the number of times the first and/or second means of purification is repeated according to the desired level of purity and yield.

In one embodiment of the present invention, a strongly basic anion exchange resin-based chromatographic column can be employed as a first means of purification. In another embodiment, the first means of purification can be a strongly basic (type I) anion exchange resin, for example, for decolorizing intermediate to light solutions, and removing metal ions. In another embodiment, the first means of purification can be an Amberlite® IRA-900 or an equivalent column thereof. The IRA-900 column is a strongly basic, macroreticular resin of moderately high porosity with benzyltrialkylammonium functionality which is useful in decolorizing and removal of organic materials. The matrix is made of styrenedivinylbenzene (macroreticular) with a particle size of 16 to 50 mesh. In another embodiment, the first means of purification can be an Amberjet® 4200 or 4600 column. In general, this chromatographic step removes the pigments from the extract. These pigments can then be eluted if desired by the addition of, for example, HCl (e.g., 1N HCl, 2 bed volumes or 2 column volumes) and ethanol (e.g., 94%) to the column.

According to the present invention, a polymeric adsorbent resin or column exhibiting non-polar or hydrophobic behavior can be used as a second means of purification. For example, an Amberlite® XAD-2 or XAD-7 resin can be used to purify the sweetening compounds. An XAD-2 column is a hydrophobic crosslinked polystyrene copolymer resin, supplied as 20-60 mesh size white insoluble beads. According to the present invention, although both columns can be efficient and rapid for purifying the sweetening compounds of interest, an XAD-2 resin is preferred as it can provide slightly better purity (e.g., 85%) compared to the XAD-7 resin (e.g., 80%). The skilled person would understand that the present invention is not limited to only two successive purification steps. Additional purification steps, for example, by one or more of the above methods, can be included to achieve the higher desired level of purity, although the relative yield of the desired products may be sacrificed.

The compounds of interest can then be eluted from the second means of purification mentioned above with an appropriate elution solvent. In one embodiment, the appropriate elution solvent is a GRAS solvent or biosolvent. In another embodiment, the appropriate elution solvent is an organic certifiable solvent or biosolvent. In other (not necessarily mutually exclusive) embodiments, the appropriate elution solvent is: an alcohol or a combination of alcohols such as ethanol, sorbitol and/or mannitol; an alcohol derived from an organic plant source; and/or grape ethanol.

According to the present invention, the concentration of the appropriate elution solvent mentioned above can affect the yield of the extraction. For example, the desorption (i.e., the release or elution) of sweetening compounds and/or antioxidant compounds from the XAD-2 or equivalent gel can be affected by the presence of different concentrations of elution solvents such as ethanol. For example, according to the present invention, an 80% concentration of ethanol in the eluate (v/v) can more efficiently (e.g., more rapidly) desorb or elute sweetening compounds than a concentration of 60% ethanol (v/v). Thus, in one embodiment, a solution of about 60% to 94% of ethanol can be used for the elution. In another embodiment, a solution of about 60% or about 80% ethanol can be used for the elution. In one embodiment, the present invention provides a *stevia* extract with a purity of sweetening compounds of at least 85%. In another embodiment, the present invention provides a *stevia* extract with a purity of sweetening compounds of at least 85%, 86%, 87%, 88%, 89%, 90%, 91%, 92%, 93%, 94%, 95%, 96%, 97%, 98% or 99%. In another embodiment, a purity of about 88% can be reached. In another embodiment a purity of about 95% can be reached.

Atomization of the Organic *Stevia* Extracts of the Present Invention

The content of the sweetening and antioxidant compounds of interest can be measured, for example, by high performance liquid chromatography (HPLC) according to methods that are well known in the art.

Applications of the Present Invention

Because the organic *stevia* extract of the present invention has sweetening potential, it can be of special interest to the food industry, for example, as a food additive, a food supplement, and/or a functional food, or for the neutraceutical or pharmaceutical industry used as excipients, Furthermore, a zero calorie and sugarless extract can also be in medical food) for applications such as diabetes, obesity, metabolic conditions and chronic diseases.

The present invention is illustrated in further details by the following non-limiting examples.

EXAMPLES

Example 1

Figure 4:
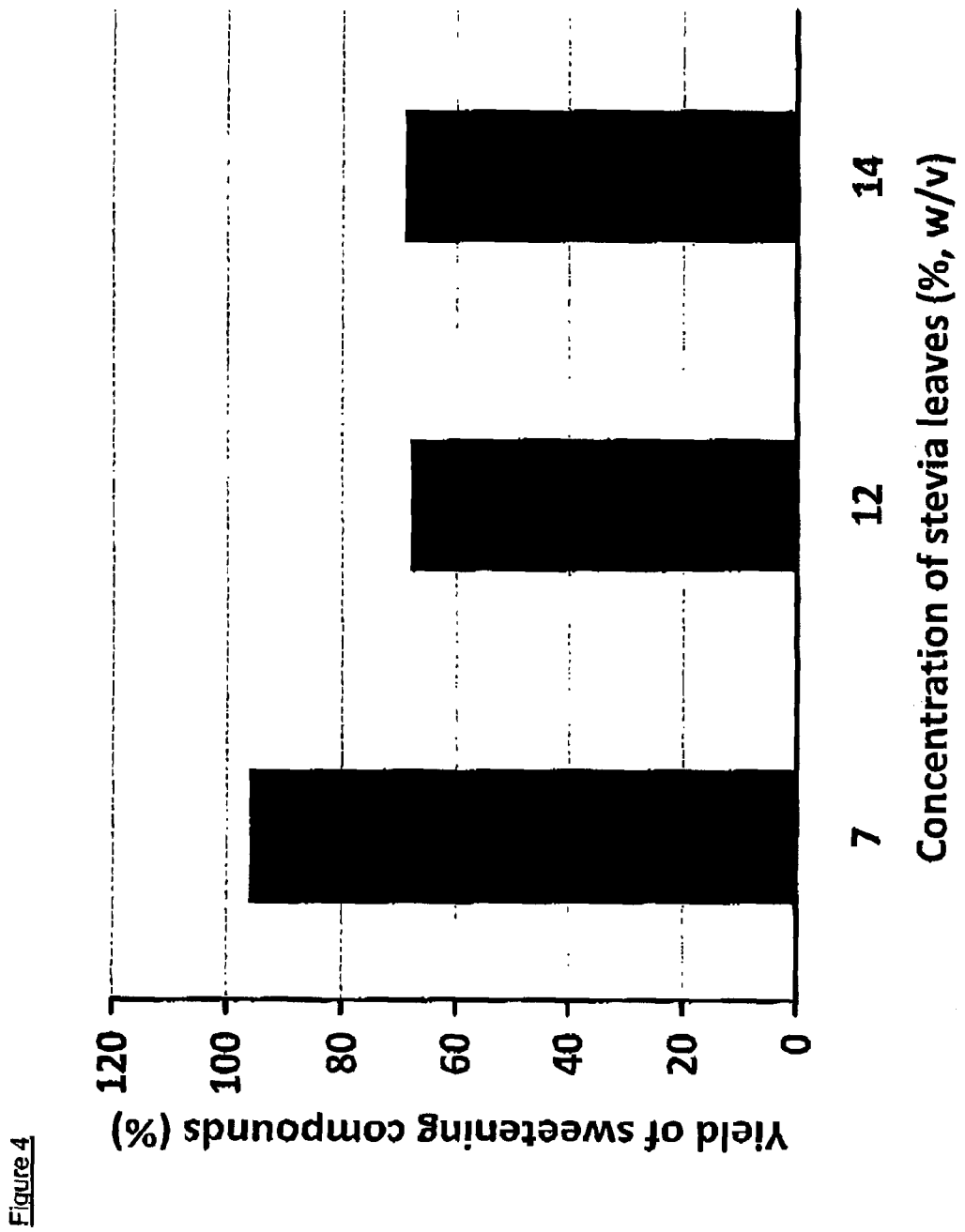
FIG. 4 shows the effect of the starting raw material concentration on the extraction yield of sweetening compounds from a water-based extraction.

Effect of Concentration of Starting Raw Material on Yield of Sweetening Compounds The effect of the raw material concentration (raw material to solvent ratio or percentage) on the extraction yield of sweetening compounds (i.e., stevioside and rebaudioside A) was examined. The raw material (i.e., *stevia* leaves) were collected and dried. Once dried, the leaves were grinded and subsequently heated for 4 hours at 110° C. The grinded and dried leaves were then subjected to two hot water extractions: the first being at a temperature of 85° C. for 30 min, and the second being at a temperature of 60° C. for 30 min. FIG. 4 shows the percent yield (relative yield) following the above extraction for three different concentrations (w/v) of raw material: 7%, 12% and 14%. A starting raw material concentration of 7% resulted in the highest relative yield of sweetening compounds (i.e., over 90%) compared to starting raw material concentrations of 12% and 14% (below 75%). A starting concentration of 14%, however, resulted in a higher final concentration of sweetening compounds (123 mg/mL) compared to a starting concentration of 7% (95 mg/mL). Thus, the higher concentration of starting material (i.e., 14%), while producing a higher concentration of sweetening compounds (i.e., 123 mg/mL), resulted in a greater loss (i.e., 28%) of the desired products.

Example 2

Effect of Temperature of Extraction on Yield of Sweetening Compounds

Figure 5A:
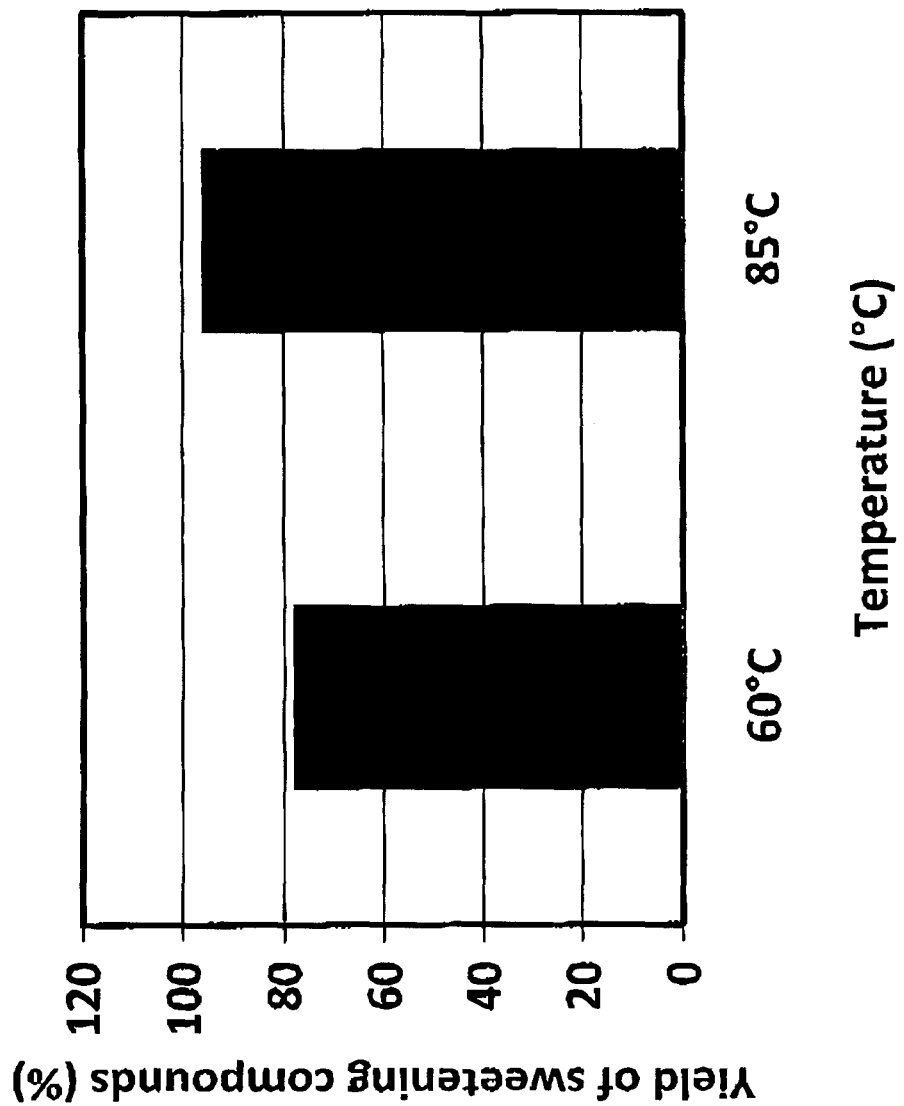
FIG. 5A shows the effect of temperature of extraction on the yield of sweetening compounds.
Figure 5B:
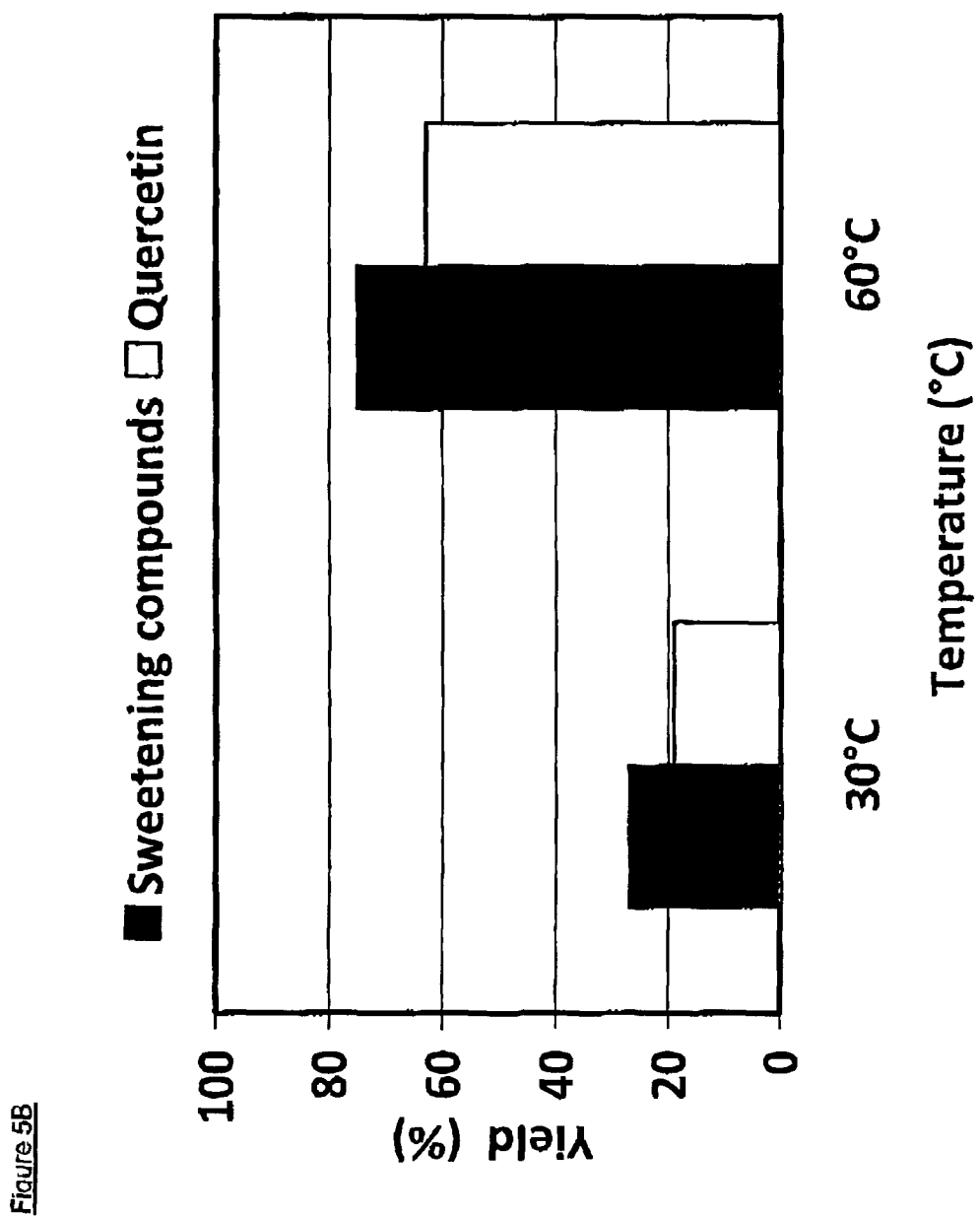
FIG. 5B shows the effect of other temperatures of extraction on the yield of sweetening compounds.

The effect of the temperature of the extraction solvent used on the extraction yield of sweetening compounds (i.e., stevioside and rebaudioside A) was examined. In the present example, double extractions were performed and a concentration of starting material of 7% (w/v) was used for each extraction. Furthermore, each extraction was performed for about 30 minutes. FIG. 5A shows the results from an extraction with water while FIG. 5B shows the results from an extraction with ethanol. In each case, the yield was calculated as follows. For the yield of sweetening compounds, the following formula was used: [quantity of steviosides+rebaudiosides in the extract]/[quantity of steviosides+rebaudiosides found in the leaves of *stevia*]×100%.

FIG. 5A shows the results from an extraction with hot water at two different temperatures. For the extraction labeled "60° C.", two successive extractions were performed in hot water, both at 60° C. For the extraction labeled "85° C.", a first extraction was performed in hot water at 85° C. and a second extraction was performed in hot water at 60° C. As shown in FIG. 5A, the double extraction with hot water comprising a first extraction at a temperature of 85° C. and a second extraction at a temperature of 60° C. resulted in a yield of 96% of sweetening compounds.

FIG. 5B shows the results from an extraction with 80% ethanol (v/v) at two different temperatures. For the extraction labeled "30° C.", two successive extractions were performed in ethanol, both at 30° C. For the extraction labeled "60° C.", two successive extractions were performed in hot ethanol, both at 60° C. As shown in FIG. 5B, the double extraction with hot ethanol at 60° C. resulted in a higher yield of sweetening compounds (black bars) compared the double extraction with ethanol at 30° C.

Example 3

Figure 6:
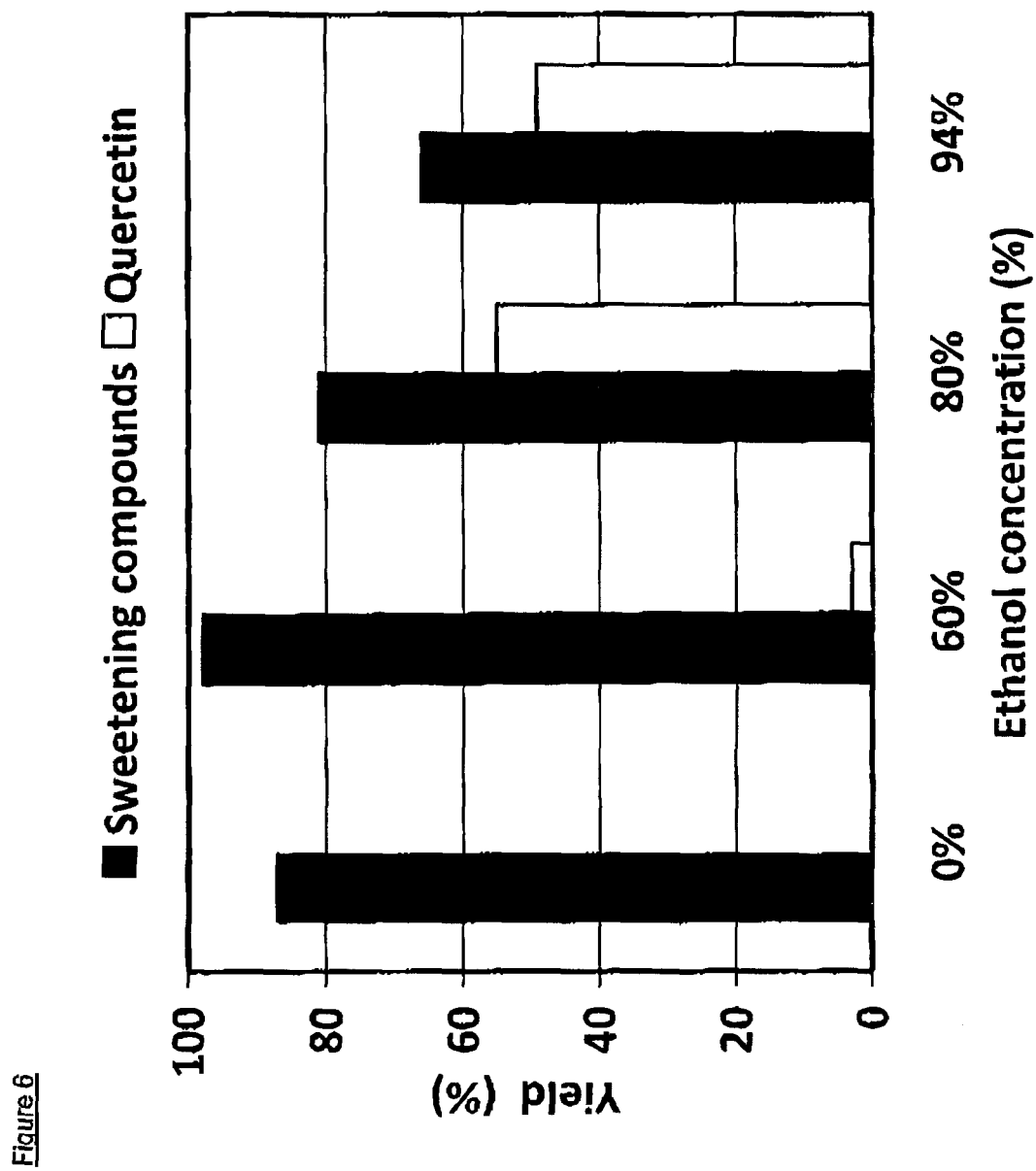
FIG. 6 shows the effect of ethanol concentration on the yield of sweetening compounds.

Effect of Ethanol Concentration on the Yield of Sweetening Compounds and Quercetin In the current example, extractions were performed and yields were calculated as described in Example 2, unless otherwise indicated. FIG. 6 shows the results from double extractions performed with increasing concentrations of ethanol on the yield of sweetening compounds (i.e., stevioside and rebaudioside A; black bars). Of the four ethanol concentrations shown in FIG. 6 (i.e., 0%, 60%, 80% and 94%), the ethanol concentration of 60% resulted in the highest yield of sweetening compounds.

Example 4

Figure 7:
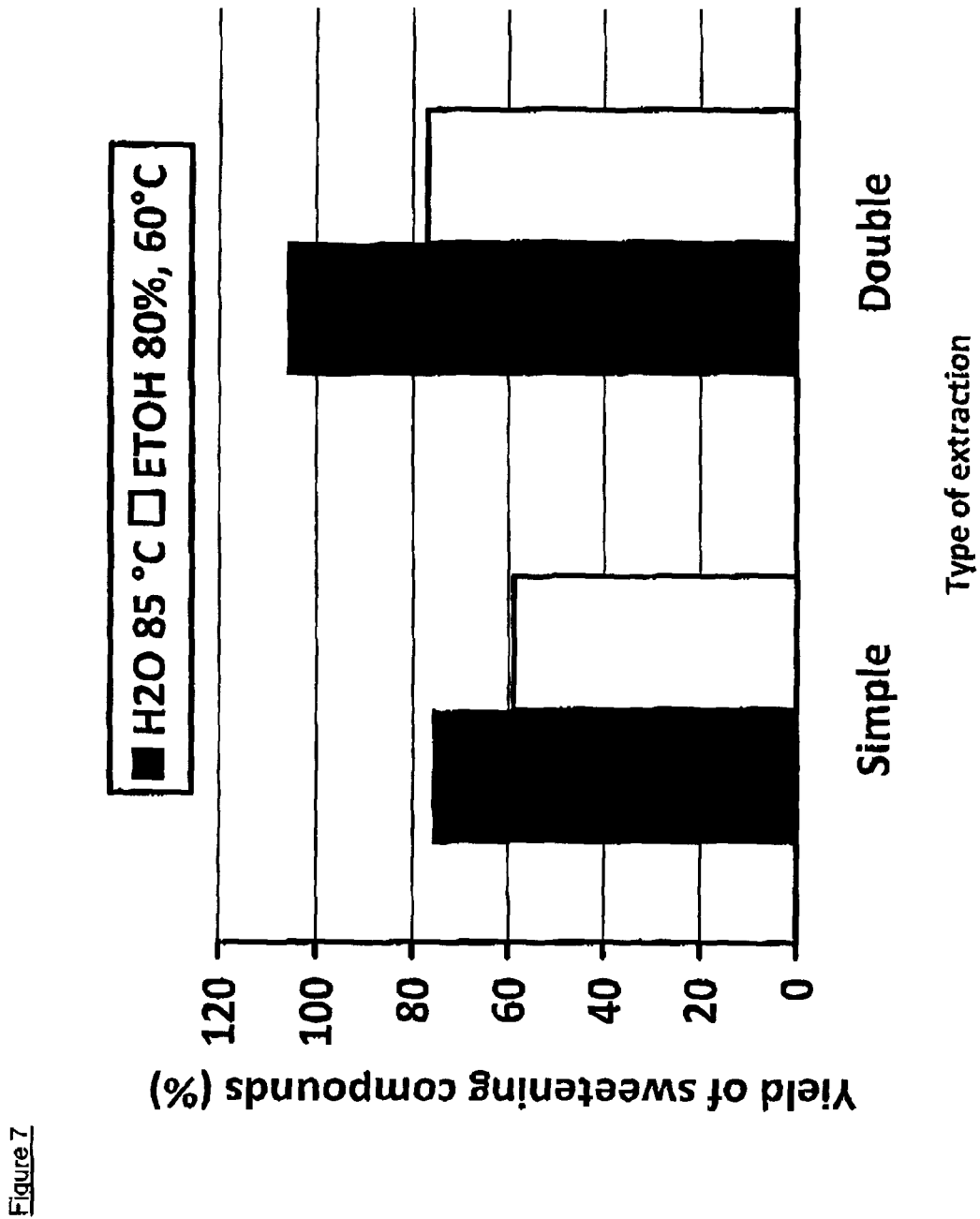
FIG. 7 shows the effect of the number of successive extractions on the yield of sweetening compounds.

Effect of the Number of Successive Extractions on Yield of Sweetening Compounds The effect of the number of successive solvent extractions performed on the extraction yield of sweetening compounds (i.e., stevioside and rebaudioside A) was examined. In the current example, extractions were performed and yields were calculated as described in Example 2, unless otherwise indicated. FIG. 7 shows the effect of simple versus double extractions on the yield of sweetening compounds. Briefly, four separate extraction strategies were tested: two water-based extractions (black bars) and two ethanol-based extractions (white bars). For the water-based simple extraction (left black bar), a single extraction in hot water at a temperature of 85° C. was performed. For the water-based double extraction (right black bar), a first extraction in hot water at a temperature of 85° C. followed by a second hot water extraction at 60° C. was performed. For the ethanol-based simple extraction (left white bar), a single extraction with 80% ethanol (v/v) was performed at a temperature of 60° C. For the ethanol-based double extraction (right white bar), two extractions with 80% ethanol (v/v) at 60° C. were performed in succession. FIG. 7 shows that that a double extraction results in a higher yield of sweetening compounds compared to a simple extraction.

As shown in FIG. 7, a double extraction (i.e., two successive extractions) increased the relative yield of both sweetening compounds by 25-30%.

Example 5

Effect of Multiple Successive Extractions using Combinations of Different Solvents on Yield of Sweetening Compounds and Quercetin In this example, a concentration of starting material of 7% (w/v) was used and each extraction was performed for 30 minutes. Yield of sweetening compounds and quercetin were calculated as described in Example 2.

Figure 8:
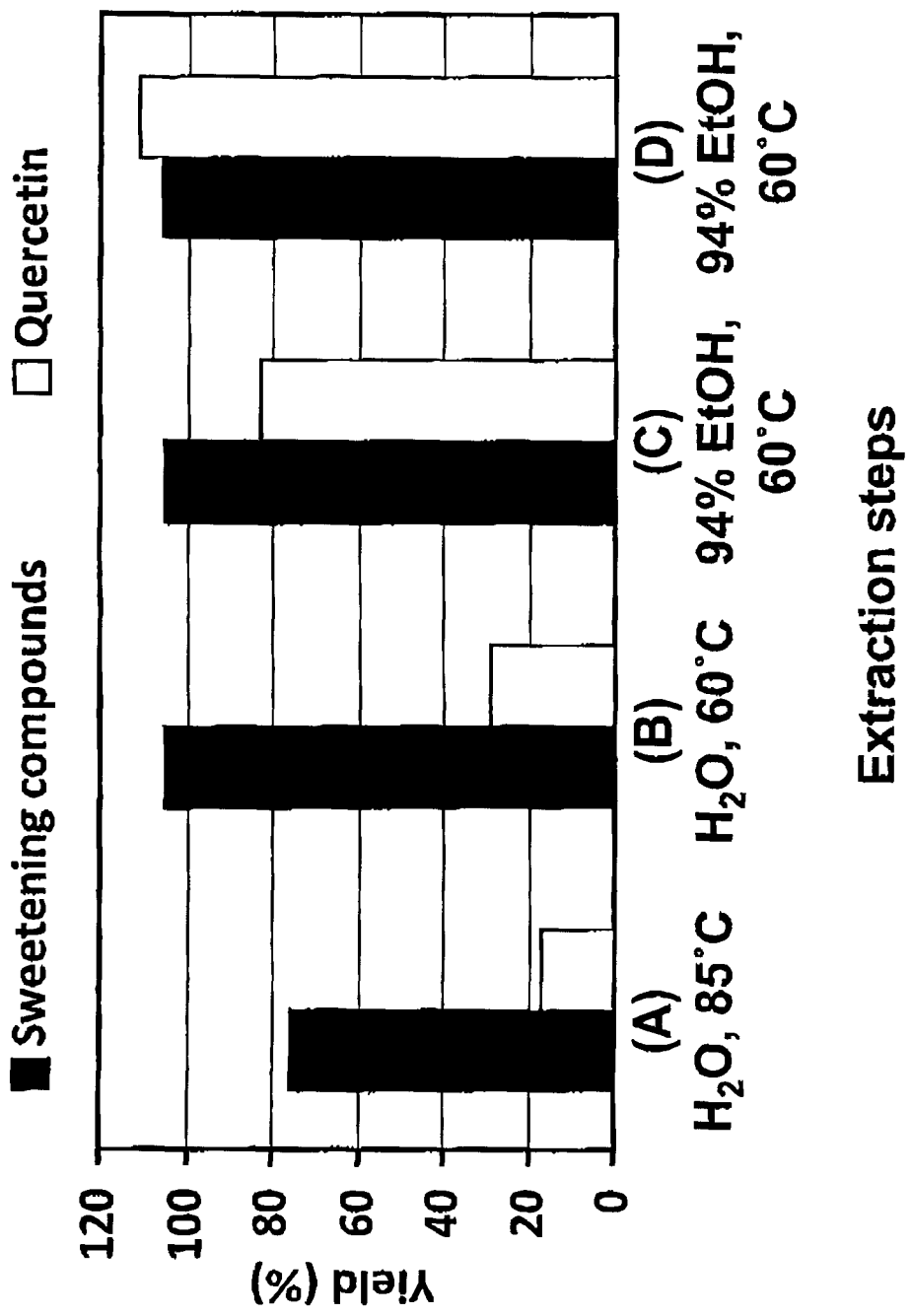
FIG. 8 shows the effect on yield of sweetening compounds (black bars) following a water-ethanol four-step extraction process.
Figure 9:
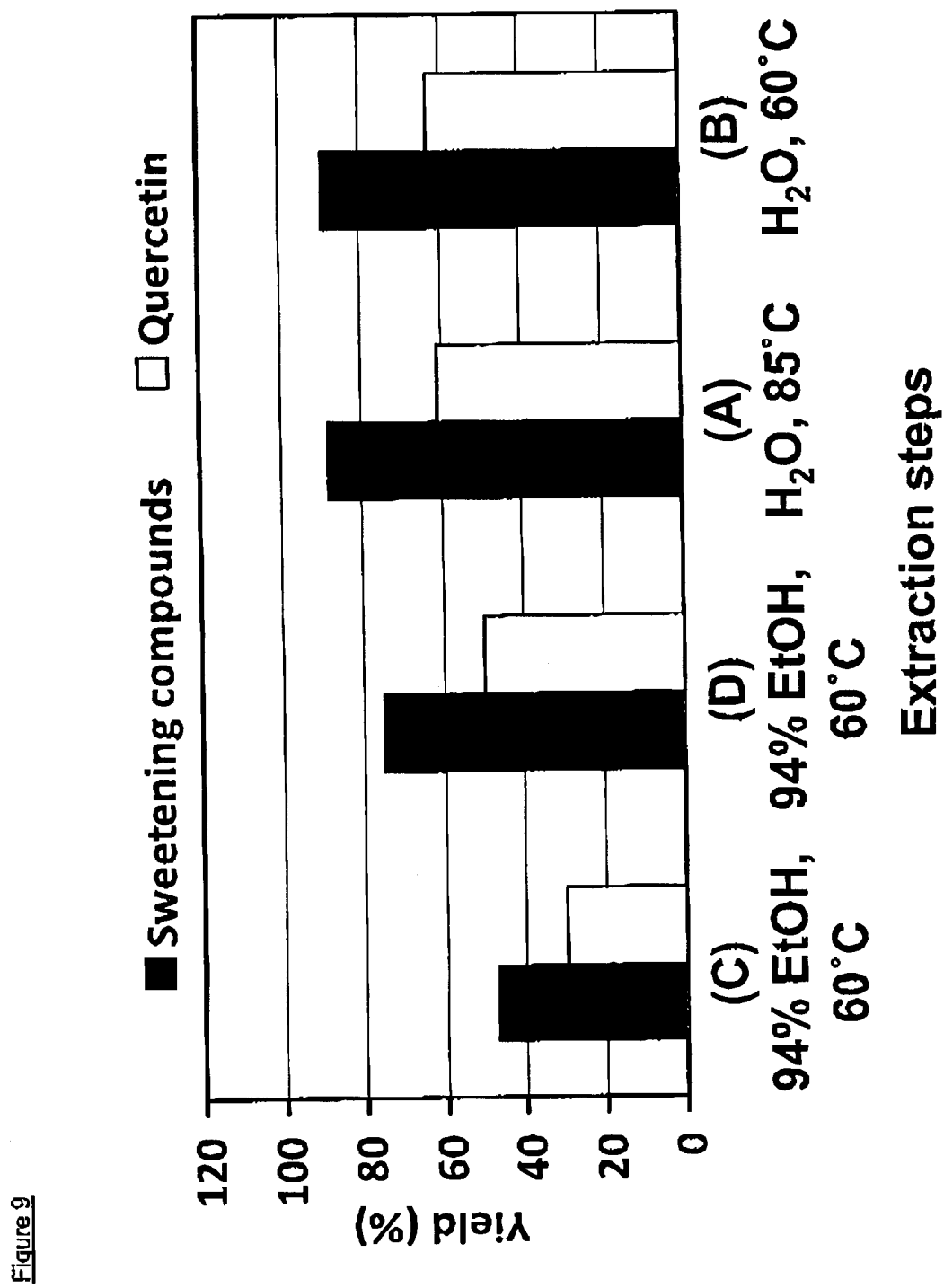
FIG. 9 shows the effect on yield of sweetening compounds (black bars) following an ethanol-water four-step extraction process.
Figure 10:
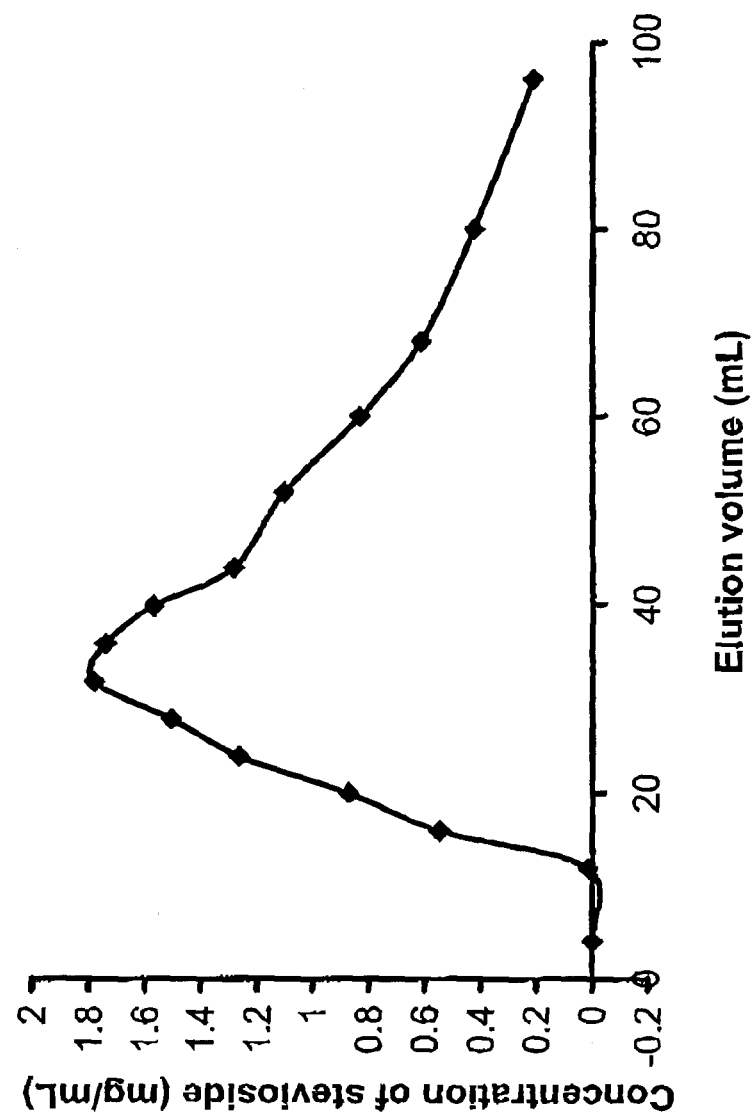
FIG. 10 shows the concentration of sweetening compounds in the flow through (eluate) following purification with an IRA-900 column as a function of the volume of water extract applied to the column.

FIGS. 8 and 9 show the effect on yield of sweetening compounds (black bars) following each step of a four-step extraction process. In both of these figures, step "(A)" involves an extraction performed with hot water at 85° C.; step "(B)" involves an extraction performed with hot water at 60° C.; and steps "(C)" and "(D)" both involve an extraction performed with hot ethanol at 60° C. In FIG. 10, the two hot water-based extraction steps ("(A)" and "(B)") were performed followed by the two hot ethanol-based extraction steps ("(C)" and "(D)"). Conversely, in FIG. 11, two hot ethanol-based extraction steps ("(C)" and "(D)") were performed followed by two hot water-based extraction steps ("(A)" and "(B)").

As shown in FIGS. 8 and 9, multiple successive extractions using combinations of different solvents can increase the yield of both sweetening compounds compared to the use of a single type of solvent. Furthermore, an extraction process comprising two hot water-based extraction steps followed by two hot ethanol-based extraction steps (FIG. 8) provided a higher yield of sweetening compounds than an extraction process involving the reverse sequence (FIG. 9.

Example 6

Purification of Sweetening Compounds with IRA-900 and XAD Columns

Two successive chromatographic purifications using different gel columns were employed to purify the sweetening compounds of interest (i.e., stevioside and rebaudioside A) from a water-based extract of the present invention. A concentration of starting material of 7% (w/v) was used for the extraction and a double extraction in water for 30 minutes was performed: the first at a temperature of 85° C. and the second at a temperature of 60° C. The yield of sweetening compounds was calculated as described in the previous examples. Following extraction, the first purification was done with an Amberlite® IRA-900 column (2 cm diameter×35 cm length) to remove the pigments from the water-based extract, which remain fixed on the resin in the column. The flow rate of the water-based extract through the column was adjusted to 4 mL/min. Different volumes of the water-based extract were allowed to flow though the column. As shown in FIG. 10, a volume of 35 mL resulted in the maximum concentration of sweetening compounds in the eluate. A volume of 100 mL enabled the recovery of 90% of the sweetening compounds and a removal of the pigments from the extract.

Following the flowthrough of the water-based extract, the pigments were then removed from the IRA-900 column with 1 N HCl and ethanol (94%).

Figure 11:
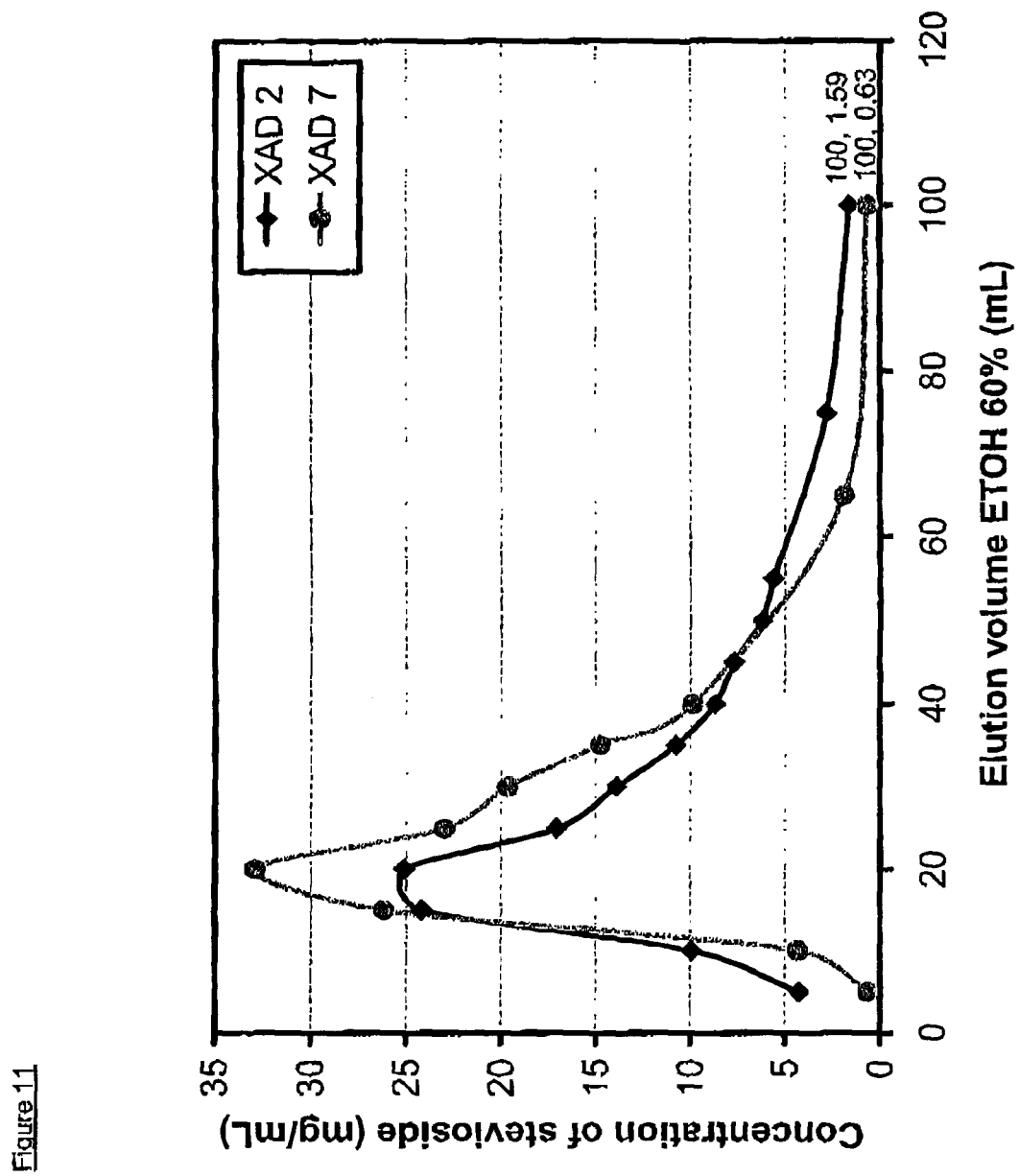
FIG. 11 shows a comparison of elution profiles for the sweetening compounds when an XAD-2 or XAD-7 column is used for the purification and a 60% ethanol solution is used for elution.

The second step of the purification was done using a XAD-2 column on which the sweetening compounds and the antioxidant compounds were retained. FIG. 11 shows the elution profile of sweetening compounds eluted from two different columns: XAD-2 and XAD-7. For each case, a solution of 60% ethanol was used as the eluate. As shown in FIG. 11, the two elution profiles were similar, suggesting that a consideration of other parameters, such as yield and purification rate, can influence the choice of one column over the other. A person of skill in the art will be able to adapt the purification means to meet particular needs of yield, rate, purity, etc.

Example 7

Figure 12:
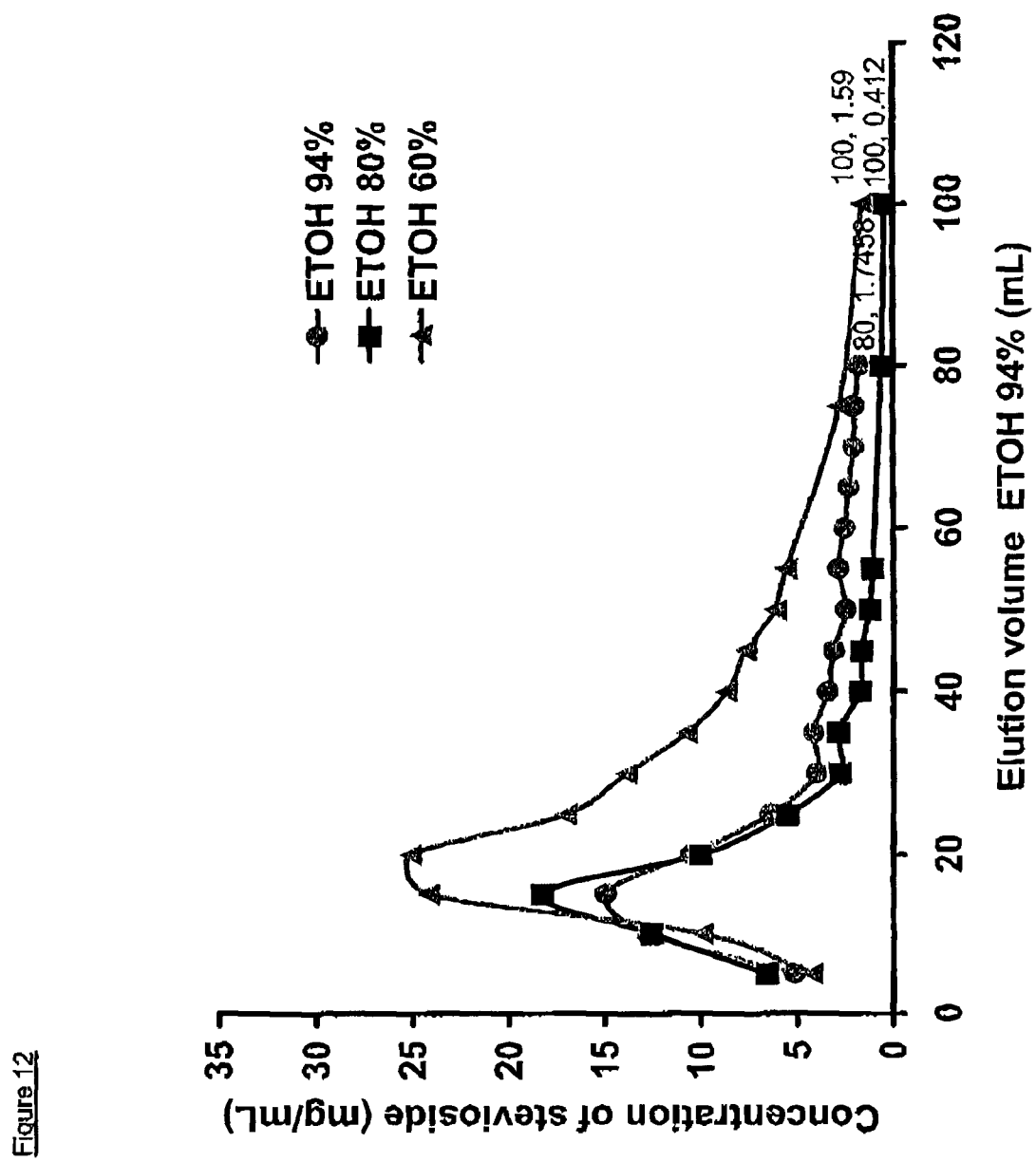
FIG. 12 shows the effect of the concentration of ethanol in the eluate on the desorption of sweetening compounds from an XAD-2 column.

Effect of the Concentration of Ethanol in the Eluate on Desorption of Sweetening Compounds from an XAD-2 Column The effect of the concentration of ethanol in the eluate on desorption of sweetening compounds (i.e., stevioside and rebaudioside A) was examined. Different concentrations of ethanol were tested. According to the results presented in FIG. 12, an 80% ethanol eluate solution was superior to solutions of 60% and 94% ethanol, since it allowed for a more a rapid desorption of the sweetening compounds.

Example 8

Comparison of XAD-2 and XAD-7 Columns for Purifying Sweetening Compounds

A concentration of starting material of 7% (w/v) was used for the extraction and a double extraction in water for 30 minutes was performed: the first at temperature of 85° C. an the second at a temperature of 60° C. The yield of sweetening compounds was calculated as described in the previous examples. Following purification with the IRA-900 column (as described in the previous example), the water-based extract was purified with either an XAD-2 column or an XAD-7 column. Although both resins/columns can be efficient and rapid for purifying the sweetening compounds, the XAD-2 resin is preferred over an XAD-7 resin as it can provide slightly better purity (e.g., 85%) compared to the XAD-7 resin (e.g., 80%).

Example 9

Figure 13:
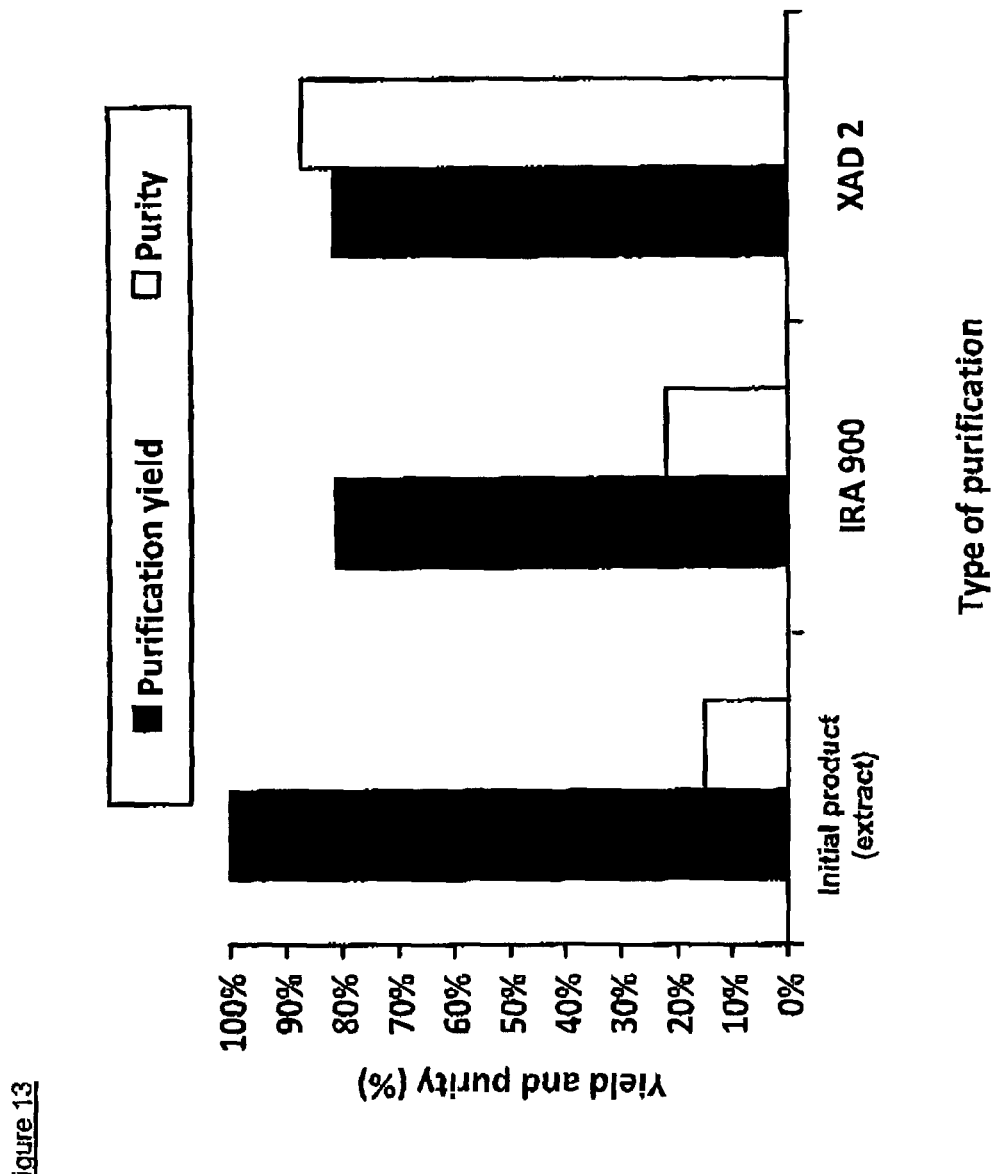
FIG. 13 shows the effect of successive purifications with IRA-900 and XAD-2 columns on yield and purity of the sweetening compounds.

Effect of Successive Purifications with IRA-900 and XAD-2 Columns on Yield and Purity of Sweetening Compounds This example shows the increase in the purity of sweetening compounds by employing a second purification step with an MD-2 column as well as the minimal loss in yield. A concentration of starting material of 7% (w/v) was used for the extraction and a double extraction in water for 30 minutes was performed: the first at temperature of 80° C. an the second at a temperature of 60° C. The yield of sweetening compounds was calculated as described in the previous examples. As shown in FIG. 13, the purity of the extract of the present invention for sweetening compounds (i.e., stevioside and rebaudioside A) is increased following a first purification step with an IRA-900 column, followed by a second purification step with an MD-2 column. More particularly, as can be seen in FIG. 13, the initial extract had a starting purity of sweetening compounds of 15%. This purity increased to 22% following the first purification step with the IRA-900 column, concomitant with an observed loss of 19%. The second purification step with the MD-2 column increased the purity to 87% without a significant further loss of sweetening compounds. Of the 13% remaining impurities, 1% consisted of quercetin and 12% of unknown compounds. The yield after the first and second purification steps remained above 80%.

Example 10

Figure 14:
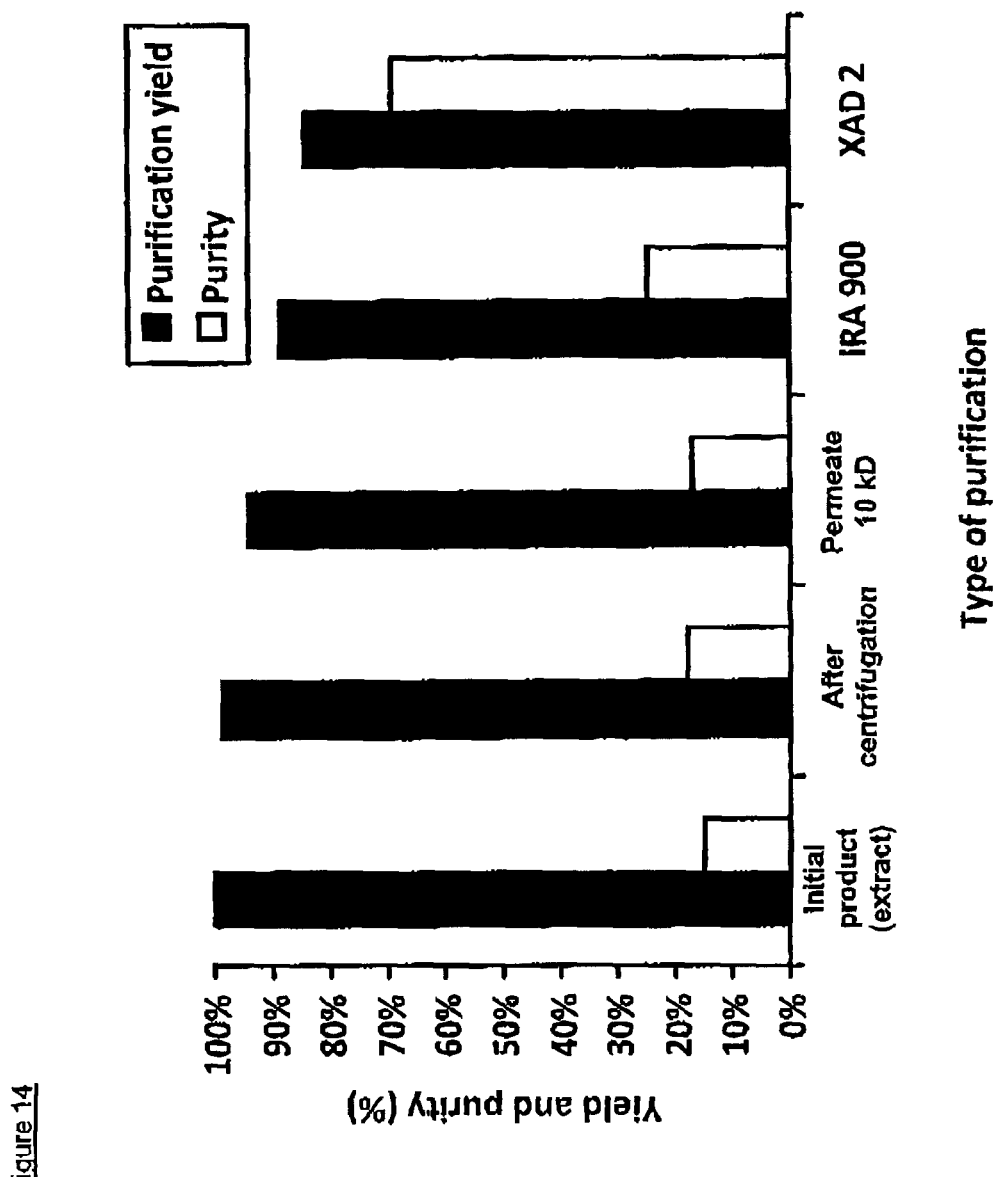
FIG. 14 shows the effect of the ultrafiltration on yield and purity of the sweetening compounds.

Effect of the Ultrafiltration or Centrifugation on Yield and Purity of Sweetening Compounds As can be seen in FIG. 14, when an additional step of continuous centrifugation at 2 000 g and diafiltration (50% of initial volume was added to the retentate using water as a solvent and a 2 kD nitrocellulose membrane or a 10 kD polysulfone membrane was used for ultrafiltration) was employed before purification of the water-based extracts with the IRA-900 column, the extract was clarified but these additional steps did not greatly improve the purity.

Example 11

Content of Sweetening and Antioxidant Compounds Measured by High Performance Liquid Chromatography (HPLC)

Sweetening compounds were separated and quantified using an inverse phase column (C18, 5 μm, 250×4.6 mm). The mobile phase was 68% methanol and 32% water in an isocratic mode. The chromatography was done at room temperature at the flow rate equal to 1 mL/min under a pressure of between 2500 and 2700 psi. The chromatography lasted 20 minutes and sweetening compounds (steviosides and rebaudioside A) had a retention time of 15.4 minutes. The standard used was obtained from Chromadex®.

Example 12

Figure 15:
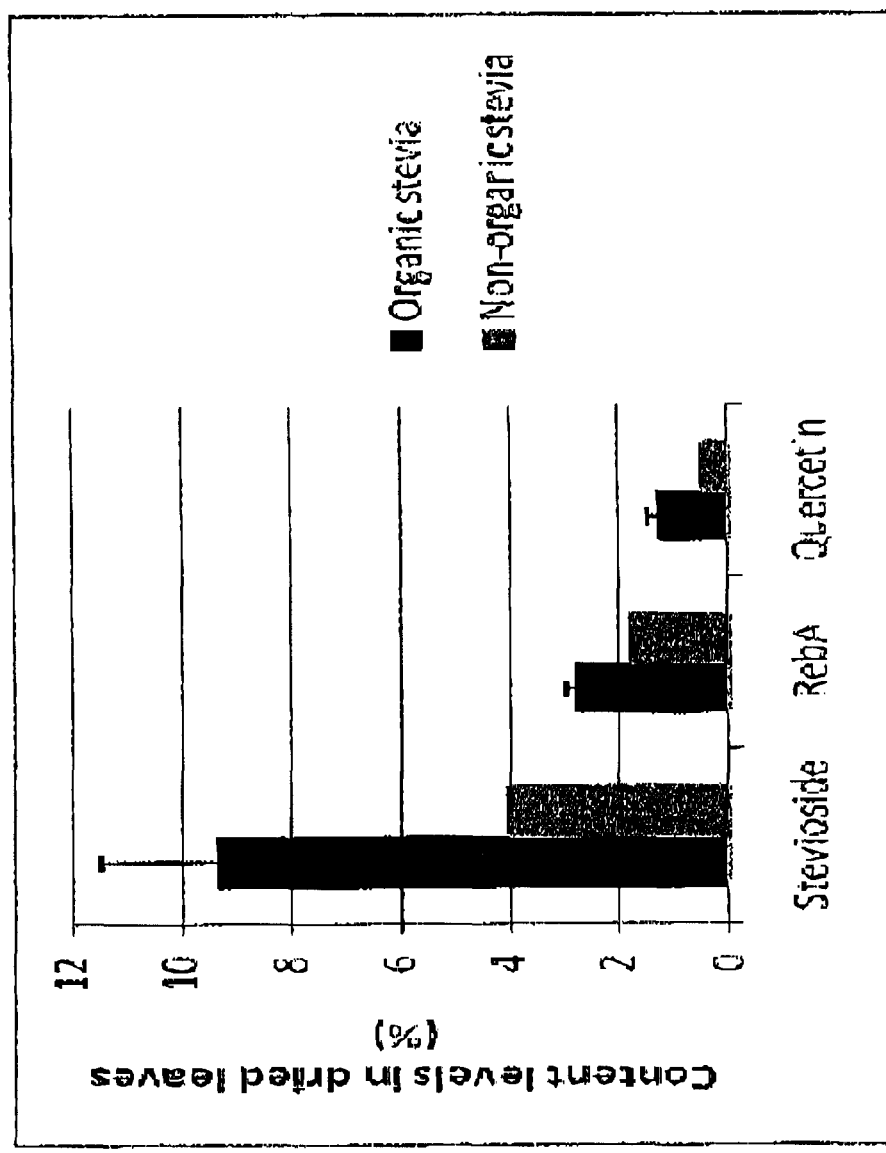
FIG. 15 shows the content levels (%) of stevioside, rebaudioside A (Reb A), and quercetin in *stevia* leaves grown organically or not.

Comparison of the Relative Amount of Compounds of Interest from Stevia Plant Sources Grown Organically or Not The growing conditions of the *stevia* plants (e.g., organic versus non-organic) can affect the content of secondary metabolites such as stevioside and quercetin present therein. Our data shows that stevioside concentrations are significantly increased when *stevia* plants are grown in organic conditions. In this regard, FIG. 15 shows the content levels (%) of stevioside, rebaudioside A (Reb A), in *stevia* leaves grown organically or not.

Although the present invention has been described hereinabove by way of specific embodiments thereof, it can be modified, without departing from the spirit and nature of the subject invention as defined in the appended claims.

Example 13

Effects of Electrocoagulation on Solution Clarity

The effect of electrocoagulation on clarifying the solution to be treated was verified by following the absorbance of the solution at 410nm and at 630 nm during 7 hours of electrolysis. The following table summarizes the data of this experiment:

TABLE 4

| Time in minutes<br>Temps en nm<br>électrolyse | Current intensity<br>in Amps<br>Intensité du courant<br>en Ampère | Absorbance<br>410 nm | Absorbance<br>630 nm |
|---|---|---|---|
| 0 | 2.8 | 3.436 | 0.260 |
| 40 | 2.8 | 3.56 | 0.325 |
| 77 | 2.76 | 3.427 | 0.234 |
| 167 | — | 3.319 | 0.213 |
| 307 | 1.48 | 1.54 | 0.059 |
| 357 | 1.22 | 1.372 | 0.057 |
| 417 | 1.2 | 1.26 | 0.056 |

Volume to be treated = 1.800 ml; NaCl = 1.85 g; surface of aluminum anode = 182 $cm^2$; surface of aluminum cathode = 580 $cm^2$; current intensity = 2.8 A to 1.2 A.

Figure 16:
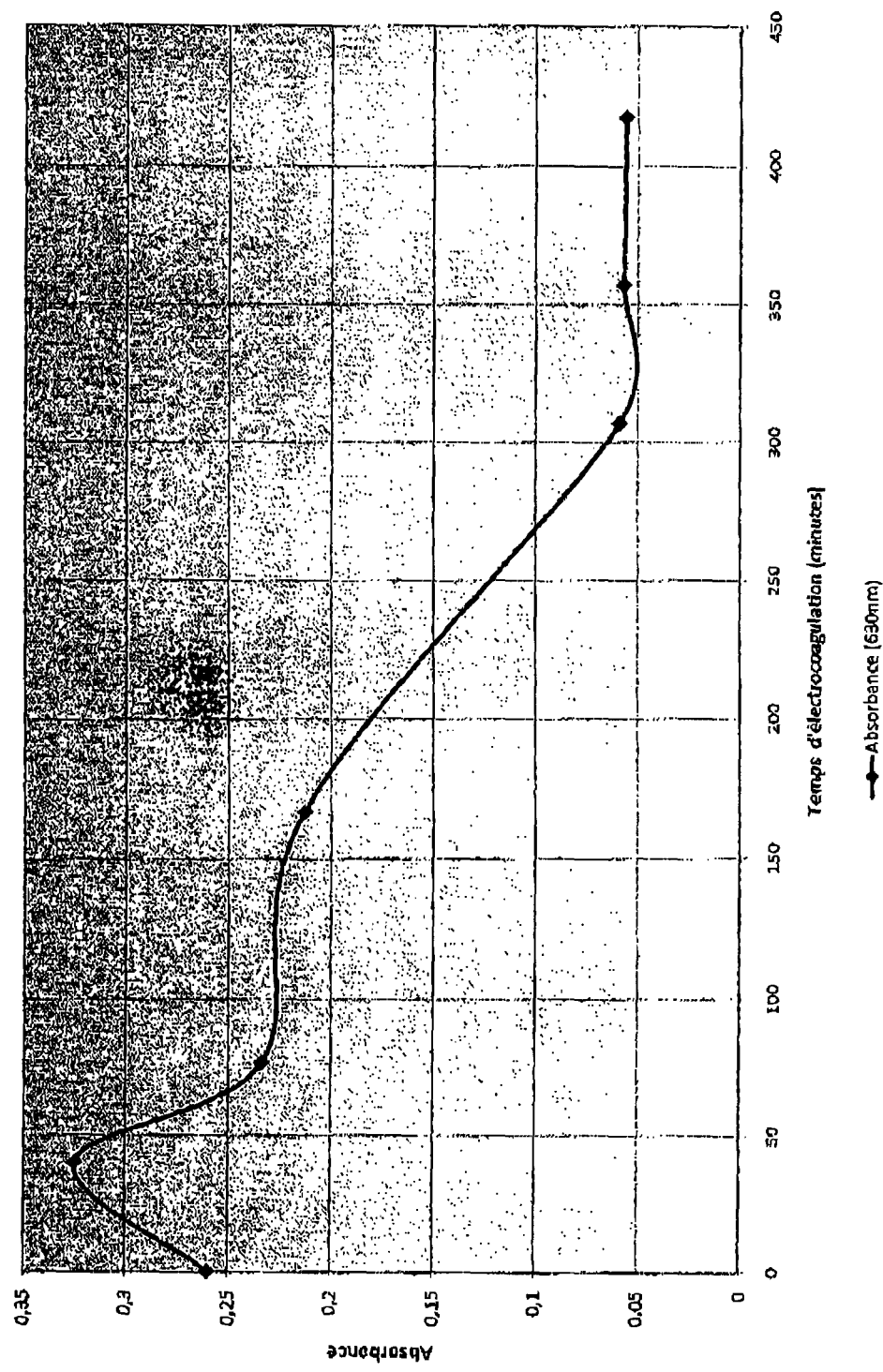
FIG. 16 shows the variation of absorbance at 630nm as a function of time of electrocoagulation.

This data demonstrates that the absorbance at 410nm and at 630nm diminish as a function of time (see FIG. 16). The solution treated clears out. After 7 hours of electrolysis, the coagulate thus formed can be separated from the liquid. The solution thus obtained is still greenish but is exempt of matter in suspension and many undesirables substances. The step of electrocoagulation is also very useful prior to the filtration step on the anion exchange resin (IRA-900). Depigmentation is made easier and the column may be reused several times. However, a certain loss of sweetening substances was noticed during this step, a fact that may affect the final yield of the purification method.

Example 14

In summary, the efficiency of each step of this process range from 80 to 98% (see Table 5).

TABLE 5

| Process efficiency for extraction of organic *stevia* | | |
|---|---|---|
| Step 1: Extraction | Aqueous extraction with specific conditions | 88-95% efficiency |
| Step 2: Primary purification | Electrocoagulation with specific condition | 93-94% efficiency |
| Step 3: Secondary purification | Membrane chromatography using ion-exchange resin IRA-900 | 97-98% efficiency |

TABLE 5-continued

Process efficiency for extraction of organic stevia

| Step 4: Tertiary purification | Membrane chomatography using XAD-2 and organic ethanol for elution | 80-90% efficiency |
| Step 5: Drying | Heat drying for lab scale or spray drying for industrial scale | 93-97% efficiency |

Table 6 shows different embodiments of the process of the invention carried under varying conditions. Particularly, it can be seen that the conditions of the specific steps may vary and be adjusted according to the skill of one in the art and obtain highly purified stevia extract.

TABLE 6

| # sample | % steviol glycoside | % Stevioside | % Reb A | % Reb C | Raw material used | color | Conditions of extraction |
|---|---|---|---|---|---|---|---|
| EC20101020-05 | 96.18 | 66.47 | 23.55 | 6.16 | Stevia Bio La Pocatière 26-9-08 | white | Extraction 85° C. and 65° C. Electrocoagulation TP ° C., of 3.8 to 1.2 A for 8 hours Filtered 11 um pH adjust 7, IRA 900 (500 ml/100 g) pH 6, XAD2 (825 ml/100 g) Heat dryingn at 80° C. |
| EC20101020-06 | 93.26 | 65.67 | 21.04 | 6.55 | Stevia Bio La Pocatière 26-9-08 | pale yellow | Extraction 85° C. and 65° C. Electrocoagulation TP ° C., of 3.8 to 1.2 A for 8 hours Filtered11 um IRA 900 not performed pH 6, XAD2 (500 ml/100 g) Heat drying at 80° C. |
| EC20101111-05 | 97.66 | 68.70 | 23.00 | 5.96 | Stevia Bio La Pocatière 26-9-08 | white | Extraction 85° C. and 65° C. Electrocoagulation TP ° C., dof 3.1 to 2.45 A for 8 ours Filtered11 um pH 7 adjust, IRA 9 (1000 ml/100 g) pH 6, XAD2 (1280 ml/100 g) Heat drying at 80° C. |
| EC20110104-07 | 98.40 | 10.17 | 80.21 | 8.02 | Crazysweet | white | Extraction 85° C. and 65° C. Electrocoagulation TP ° C., of 2.7 A for 8 hours Filtered 11 um pH 7 adjust IRA 900 (830 ml/100 g) pH 6, XAD2 (1000 ml/100 g) Heat drying at 80° C. |
| EC20110104-10 | 94.44 | 10.64 | 76.51 | 7.29 | Crazysweet | white | Extraction 85° C. and 65° C. Electrocoagulation TP ° C., of 2.7 A for 8 hours Filtered 11 um pH 7 adjust, IRA 900 (850 ml/100 g) pH 6, XAD2 (950 ml/100 g) Heat drying 80° C. |
| EC20110418-05P | 97.8 | 69.3 | 19.9 | 6.8 | Stevia Bio La Pocatière 26-9-08 | white | Extraction 85° C. and 65° C. Electrocoagulation 15 at 70° C., 3.9 to 6.5 A for 150 minutes Filtered 11 um (hot) pH 7 adjust IRA 900 (2300 ml/100 g) pH 6, XAD2 (2500 ml/150 g) Heat drying at 80° C. |

Solventless Alternative:

It is also possible to carry out the process described herein while using no solvent other than water. This process uses a series of consecutive filtrations with specific molecular-weight cut-off (microfiltration, ultrafiltration and/or nanofiltration) instead of the hydrophobic or non-polar chromatography of step (c). With this alternative embodiment, the stevia extraction process is entirely "solvent-free". Particularly, this alternative step is carried out with ultrafiltration membranes, particularly having MWCO of between 600 to 10,000 Da.

Energy-Saving Alternative:

Alternatively, the electrocoagulation step may be replaced with a step of successive filtrations with membranes of specific molecular weight cut-off (nanofiltration, microfiltration, ultrafiltration) to minimize the electrical energy used in this process. Particularly, this alternative step is carried out with ultrafiltration membranes, particularly having MWCO of between 600 to 10,000 Da.

SUMMARY AND CONCLUSION

In summary, the extraction process of the present invention can achieved high yields of high purity stevia extract of high sweetness with no or little solvent that can be characterized as "organic certifiable". The thus obtained stevia extract has high sweetness with a purity of sweetening compounds of at least 90%, but preferably 95% to meet the standards or the industry.

This process has the advantage of limited use of chemicals that can also be translated into the conventional stevia market if non-organic raw materials are used.

Although the present invention has been described hereinabove by way of specific embodiments thereof, it can be modified, without departing from the spirit and nature of the subject invention as defined in the appended claims.

REFERENCES

Adduci et al., J. Sci. Soc. Thailand 13, 179 (1987).
Bridel and Lavieille, Bull. Soc. Chim. Biol. 13, 781 (1931).
Bridel and Lavieille, Bull. Soc. Chim. Biol.13, 636 (1931).
Carlo et al., "Rapport de recherche bibliographique-Rapport d'étude" (2002).
Chang and Huang, Recent advances in food science and technology, 484 (1980).
Cheng and Chang, Journal of the Chinese Agricultural Chemical Society 23, 178 (1985).
Chun et al., J Nutr. 138(4):753-60 (2008).
Crammer and Ikan, Chem. Brit. 22, 915 (1986).
Crammer and Ikan, Progress in the Chemistry and Properties of Rebaudiosides, In:
Developments in Sweeteners, Vol. 3, ed. T. H. Grenby. Elsevier Applied Science, London, (1987).
Dobberstein and Suzuki, U.S. patent, Ed. (Stevia Company, Inc. (Arlington Heights, Ill.), 1986.
Fuh et al., Journal of food science 55, 1453 (1990).
Ghanta et al., J Agric Food Chem. 55, 10962 (2007).
Jaitak et al., Phytochem Anal 20, 240 (2009).
Jakinovich et al., J Nat Prod 53, 190 (1990).
Kinghorn and Soejarto, "Economic and medical plant research", H. H. H. Wagner, & N. R. Farnsworth, Ed. (London: Academic Press., 1985), vol. 1, pp. 1-52.
Kinghorn, A D. "Food Ingredient Safety Review: Stevia rebaudiana leaves" Herb Research Foundation, USA. (1992).
Kitahata et al., Agric Biol Chem 53, 2923-2928 (1989).
Kutowy et al., U.S. Pat. No. 5,972,120 (1998).
Liu et al., Desalination 83, 375 (1991).
Lobov et al., Agric Biol Chem 55, 2959-2965 (1991).
Nam et al., "Naturally occurring NF-kappaB inhibitors", Mini Rev Med Chem 6(8):945-951.
Nuutila et al., Food Chem. 76, 519 (April 2002).
Pasquel et al., Braz J Chem Eng 17, 271-282 (2000).
Phillips, K. C., "Developments in Sweeteners" T. H. Grenby, Ed., (Elsevier, New York, 1987), vol. 3, pp. 1-65.
Pol et al., "Comparison of two different solvents employed for pressurised fluid extraction of stevioside from Stevia rebaudiana: methanol versus water." Anal Bioanal Chem 388, 1847-1857 (2007).
Rajbhandari and Roberts, Journal of natural products 42, 194 (1979).
Shi et al., Reactive and functional polymers 50, 107 (2002).
Shoji et al., Japanese Patent JP 77-95407 (1999).
Soejarto et al., Econ. Bot. 37, 71 (1983).
Tadhani et al., J. Food Comp. Analysis. 20, 323 (2007).
Tan et al., "Isolation of sweetener from Stevia rebaudiana" Jpn. Kokai, 63, 177, 764 (1988).
Tsanava et al., Chemical Abstracts 116, 82387g (1991).
"Vaher and Koel, ""Separation of polyphenolic compounds extracted from plant matrices using capillary electrophoresis""".
J Chromatogr A. 21; 990(1-2):225-30 (2003)."
Wallin, H., "Steviol glycosides—Chemical and technical assessment", Review for the 63rd JECFA (2004).
Wood et al., J Org Chem 20, 875-883 (1955).
Xi et al., Nippon Kagaku Kaishi 45, 317 (1998).
Yamamoto et al., Biosci Biotechnol Biochem 58, 1657-1661 (1994).
Yokoyama et al., J. Japan. Soc. Food Sci. Tech. 37, 899 (1990).

The invention claimed is:

1. A method for preparing a *stevia* leaf extract, said method comprising, sequentially:
   (a) performing at least a first hot water extraction at a temperature of at least 65° C. on a dried and grinded preparation of *stevia* leaves to form a crude *stevia* leaf extract solution;
   (b) performing electrocoagulation on said crude *stevia* leaf extract solution to yield a clarified *stevia* leaf extract solution, and
   (c) removing pigments from said clarified *stevia* leaf extract solution by contacting the clarified *stevia* leaf extract solution with a strongly basic anion exchange resin to yield the *stevia* leaf extract.

2. A method for isolating sweetening compounds from the *stevia* leaf extract prepared according to the method of claim 1, comprising conducting steps (a)-(c) of claim 1 and further comprising the step of:
   (d) isolating said sweetening compounds by contacting the *stevia* leaf extract of step (c) of claim 1 with a hydrophobic or non-polar resin, and eluting with an elution solvent generally recognized as safe;
   thereby producing said isolated sweetening compounds.

3. The method of claim 1, wherein said electrocoagulation is carried out with two aluminium electrodes immersed in said solution.

4. The method of claim 2, wherein said step (d) is replaced with one or more steps of membrane filtration.

5. The method according to claim 4, wherein said membrane filtration is at least an ultrafiltration.

6. The method of claim 5, wherein said ultrafiltration is carried out on a membrane having a molecular weight cut-off of between 600 to 10,000 Da.

7. The method of claim 1, wherein the ratio of said preparation of *stevia* leaves to hot water is about 7% to about 14% in terms of weight to volume.

8. The method of claim 1, wherein said first hot water extraction is carried out at a temperature of about 80° C. to about 100° C.

9. The method of claim 1, wherein said first hot water extraction is performed for about 15 minutes to about 60 minutes.

10. The method of claim 1, further comprising extracting the preparation of *stevia* leaves following step (a) with a second hot water extraction to form an additional crude *stevia* leaf extract solution.

11. The method of claim 10, wherein said second hot water extraction is carried out at a temperature lower than that of said first hot water extraction.

12. The method of claim 11, wherein said second hot water extraction is carried out at a temperature below 80° C.

13. The method of claim 11, wherein said second hot water extraction is carried out at a temperature of about 50° C. to about 75° C.

14. The method of claim 11, wherein said second hot water extraction is carried out at a temperature of about 60° C.

15. The method of claim 1, wherein said strongly basic anion exchange resin in step (c) is a quaternary ammonium chloride functionalized polystyrene resin.

16. The method of claim 2, wherein said hydrophobic or non-polar resin in step (d) is a polymeric adsorbent resin.

17. The method of claim 16, wherein said polymeric adsorbent resin is a crosslinked polystyrene copolymer resin.

18. The method of claim 16, wherein said polymeric adsorbent resin is macroreticular.

19. The method of claim 18, wherein said polymeric adsorbent resin is eluted with two consecutive elutions of ethanol/water.

20. The method of claim 19, wherein said elutions are carried out consecutively with 25% and 50% ethanol.

21. The method of claim 1, wherein said clarified *stevia* leaf extract solution has a purity of sweetening compounds of at least 85%.

22. The method of claim 21, wherein said clarified *stevia* leaf extract solution has a purity of sweetening compounds of at least 90%.

\* \* \* \* \*